US009994625B2

(12) United States Patent
Shorter et al.

(10) Patent No.: US 9,994,625 B2
(45) Date of Patent: Jun. 12, 2018

(54) HSP104 VARIANTS AND USES THEREOF

(71) Applicant: The Trustees of the University of Pennsylvania, Philadelphia, PA (US)

(72) Inventors: James Shorter, Philadelphia, PA (US); Meredith E. Jackrel, Voorhees, NJ (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 447 days.

(21) Appl. No.: 14/630,785

(22) Filed: Feb. 25, 2015

(65) Prior Publication Data

US 2015/0240222 A1 Aug. 27, 2015

Related U.S. Application Data

(60) Provisional application No. 61/944,193, filed on Feb. 25, 2014.

(51) Int. Cl.
*A61K 38/46* (2006.01)
*A61K 38/00* (2006.01)
*C07K 14/47* (2006.01)

(52) U.S. Cl.
CPC .............. *C07K 14/47* (2013.01); *A61K 38/00* (2013.01); *A61K 38/46* (2013.01)

(58) Field of Classification Search
CPC combination set(s) only.
See application file for complete search history.

(56) References Cited

PUBLICATIONS

Grimminger-Marquardt et al (Review Structure and Function of the Molecular Chaperone Biopolymers vol. 93, No. 3, pp. 252-276 Published online Sep. 18, 2009).*
Gokhale et al (Modulation of Prion-dependent Polyglutamine Aggregation and Toxicity by Chaperone Proteins in the Yeast Model The journal of Biological chemistry 2005, vol. 24, issue 17, pp. 22809-22818).*
Berkowitz, L.A. et al., Application of a C. elegans dopamine neuron degen-eration assay for the validation of potential Parkinson's disease genes, Journal of Visualized Experiments, Jul. 2008, 17: e835.
Berkowitz, L.A. et al., Generation of stable transgenic C. elegans using microinjection, Journal of Visualized Experiments, Aug. 2008, 18: e833.
Cabantous, S. and Waldo, G.S., In vivo and in vitro protein solubility assays using split GFP, Oct. 2006, 3(10): 845-854.
Cao, S. et al., Torsin-mediated protection from cellular stress in the dopaminergic neurons of Caenorhabditis elegans, Journal of Neuroscience, Apr. 2005, 25: 3801-3812.
Cooper, A.A. et al., Alpha-synuclein blocks ER-Golgi traffic and Rabl rescues neuron loss in Parkinson's models, Science, Jul. 2006, 313: 324-328.
Cushman, M. et al., Prion-like disorders: blurring the divide between transmissibility and infectivity, Journal of Cell Science, Apr. 2010, 123: 1191-1201.
Cushman, M., et al., Hsp104 suppresses polyglutamine-induced degeneration post onset in a *Drosophila* MJD/SCA3 model, PLos, Sep. 2013, 9: e1003781.
Desantis, M.E. and Shorter, J., The elusive middle domain of Hsp104 and ClpB: location and function, Biochim Biophys Acta., Jan. 2012, 1823(1): 29-39.
Desantis, M.E. et al., Operational plasticity enables hsp104 to disaggregate diverse amyloid and nonamyloid clients, Cell, Nov. 2012, 151: 778-793.
Doyle, S.M. et al., Asymmetric deceleration of ClpB or Hsp104 ATPase activ-ity unleashes protein-remodeling activity, Nat Struct Mol Biol, Feb. 2007, 14(2): 114-122.
Duennwald, M.L. et al., Small heat shock proteins potentiate amyloid dissolution by protein disaggregases from yeast and humans, PLoS, Jun. 2012, 10: e1001346.
Elden, A.C. et al., Ataxin-2 interme-diate-length polyglutamine expansions are associated with increased risk for ALS, Nature, Aug. 2010, 466: 1069-1075.
Gietz, R.D. and Schiestl, R.H., High-efficiency yeast transformation using the LiAc/SS carrier DNA/PEG method, Nat. Protoc., Jan. 2007, 2(1): 31-34.
Glover, J.R. and Lindquist, S., Hsp104, Hsp70, and Hsp40: a novel chaperone system that rescues previously aggregated proteins, Cell, Jul. 1998, 94: 73-82.
Harrington, A.J. et al.., Functional analysis of VPS41-mediated neuroprotection in Caenorhabditis elegans and mammalian models of Parkinson's disease, Journal of Neuroscience, Feb. 2012, 32: 2142-2153.
Jackrel, M.E. et al., Potentiated Hsp104 Variants Antagonize Diverse Pro eotoxic Misfolding Events, Cell, Jan. 2014, 156: 170-182 and S1-S10.
Johnson, B.S. et al., A yeast TDP-43 proteinopathy model: Exploring the molecular determinants of TDP-43 aggregation and cellular toxicity, Proc. Natl. Acad. Sci., Apr. 2008, 105(17): 6439-6444.
Johnson, B.S. et al., TDP-43 is intrinsically aggregation-prone, and amyotrophic lateral sclerosis-linked mutations accelerate aggregation and increase toxicity, Jul. 2009, 284: 20329-20339.
Ju, S. et al., A yeast model of FUS/TLS-dependent cytotoxicity, PLos, Apr. 2011, 9(4): e1001052.
Lipinska, N. et al., Disruption of ionic interactions between the nucleotide binding domain 1 (NBD1) and middle (M) domain in Hsp100 disaggregase unleashes toxic hyperactivity and partial independence from Hsp70, Journal of Biological Chemistry, Jan. 2013, 288: 2857-2869.
LoBianco, C. et al., Hsp104 antagonizes ct-synuclein aggregation and reduces dopaminergic degeneration in a rat model of Parkinson disease, J. Clin. Invest., Sep. 2008, 118(9): 3087-3097.
Moreau, M.J. et al., ATPase site architecture and helicase mechanism of an archaeal MCM, Molecular Cell, Oct. 2007, 28: 304-314.
Newby, G.A. and Lindquist, S., Blessings in disguise: biological benefits of prion-like mechanisms, Trends in Cell Biology, Jun. 2013, 23(6): 251-259.

(Continued)

*Primary Examiner* — Kagnew H Gebreyesus
(74) *Attorney, Agent, or Firm* — Howson & Howson LLP

(57) ABSTRACT

Protein misfolding underpins several fatal neurodegenerative disorders. The application is directed to recombinant Hsp104 proteins comprising missense mutations aimed at correcting these events, and methods for expressing and delivering same.

17 Claims, 12 Drawing Sheets

(56) References Cited

PUBLICATIONS

Nishihara, K. et al. Chaperone Coexpression Plasmids: Differential and Synergistic Roles of DnaK-DnaJ-GrpE and GroEL-GroES in Assisting Folding of an Allergen of Japanese Cedar Pollen, Cryj2, in *Escherichia coli*, Applied and Environmental Microbiology, May 1998, 64(5): 1694-1699.
Outeiro, T.F. and Lindquist, S., Yeast cells provide insight into alpha-synuclein biology and pathobiology, Science, Dec. 2003, 302: 1772-1775.
Raviol, H. et al., Human and yeast Hsp110 chaperones exhibit functional differences, FEBS Letters, Jan. 2006, 580: 168-174.
Robberecht, W. and Philips, T., The changing scene of amyotrophic lateral sclerosis, Nat. Rev. Neurosci,. Apr. 2013, 14(4): 248-264.
Saibil, H., Chaperone machines for protein folding, unfolding and disaggregation, Nat. Rev. Mol. Cell Biol., Oct. 2013, 14(10): 630-642.
Sanchez, Y. and Linquist, S.L., HSP104 required for induced thermotolerance. Science, Science, Jun. 1990, 248(4959): 1112-1115.
Schirmer, E.C. et al., Dominant gain-of-function mutations in Hsp104p reveal crucial roles for the middle region, Mol. Biol. Cell., May 2004, 15(5): 2061-2072.
Shorter, J., Hsp104: a weapon to combat diverse neurodegenerative disorders, Neurosignals, Dec. 2008, 16: 63-74.
Shorter, J., The mammalian disaggregase machinery: Hsp110 synergizes with Hsp70 and Hsp40 to catalyze protein disaggregation and reactivation in a cell-free system, PLoS ONE, Oct. 2011, 6(10): e26319.
Shorter, J. and Lindquist, S., Hsp104, Hsp70 and Hsp40 interplay regulates formation, growth and elimination of Sup35 prions, EMBO, Oct. 2008, 27(20): 2712-2742.
Sun, Z. et al., Molecular determinants and genetic modifiers of aggregation and toxicity for the ALS disease protein FUS/TLS, PLoS Biol, Apr. 2011, 9(4): e1000614.
Tardiff, D.F. et al., ). Yeast reveal a “druggable” Rsp5/Nedd4 network that ameliorates alpha-synuclein toxicity in neurons, Science, Nov. 2013, 342(6161): 979-983.
Tessarz, P. et al., Substrate threading through the central pore of the Hsp104 chaperone as a common mechanism for protein disaggregation and prion propagation, Molecular Microbiology, Apr. 2008, 68(1): 87-97.
Vacher, C. et al., Overexpression of yeast hsp104 reduces polyglutamine aggregation and prolongs survival of a transgenic mouse model of Huntington’s disease, Human Molecular Genetics, Nov. 2005, 14(22): 3425-3433.
Weber-Ban, E.U. et al., Global unfolding of a substrate protein by the Hsp100 chaperone ClpA, Nature, Sep. 1999, 401(6748): 90-93.
Werbeck, N.D. et al., Coupling and dynamics of subunits in the hexameric AAA+ chaperone ClpB, Journal of Molecular Biology, Feb. 2008, 378(1): 178-190.
Shorter, J., Potentiated Protein Disaggregases, Graham Warren, Feb. 2013 (Presentation).
Jackrel, M.E. and Shorter, J., Engineering Enhanced Protein Disaggregases for Neurodegenerative Disease, Prion, Mar. 2015, 9(2): 90-109.
Jackrel, M.E. et al., Isolating Potentiated Hsp104 Variants Using Yeast Proteinopathy Models, Journal of Visualized Experiments, Nov. 2014, 93: e52089, http://www.jove.com/video/52089/isolating-potentiated-hsp104-variants-using-yeast-proteinopathy-models.
Torrente, M.P. et al., Suramin Inhibits Hsp104 ATPase and Disaggregase Activity, PLoS One, Oct. 2014, 9(10): e110115.
Seither, K.M. et al., Specific Aromatic Foldamers Potently Inhibit Spontaneous and Seeded Ap42 and AP43 Fibril Assembly, Biochemical Journal, Nov. 2014, 464(1): 85-98.
Gates, et al., “Ratchet-like polypeptide translocation mechanism of the AAA+ disaggregase Hsp104,” Science, Jul. 21, 2017, published online Jun. 15, 2017, 357:273-279, including Supplementary Materials pp. 1-39.

* cited by examiner

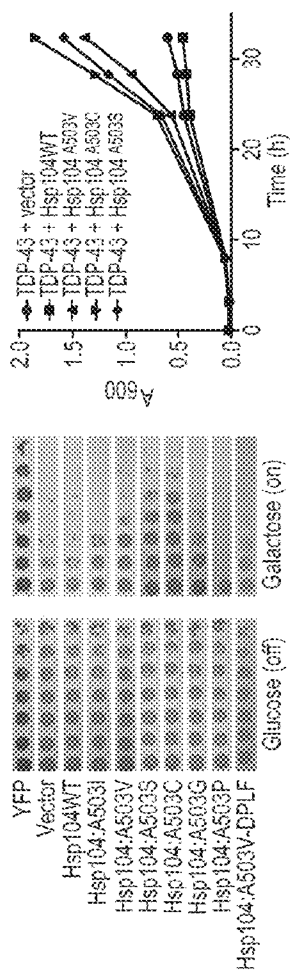
FIG. 2A
YFP
Vector
Hsp104WT
Hsp104:A503I
Hsp104:A503V
Hsp104:A503S
Hsp104:A503C
Hsp104:A503G
Hsp104:A503P
Hsp104:A503V-DPLF
Glucose (off)
Galactose (on)
FIG. 2B
TDP-43 + vector
TDP-43 + Hsp104WT
TDP-43 + Hsp104 A503V
TDP-43 + Hsp104 A503C
TDP-43 + Hsp104 A503S
A600
Time (h)

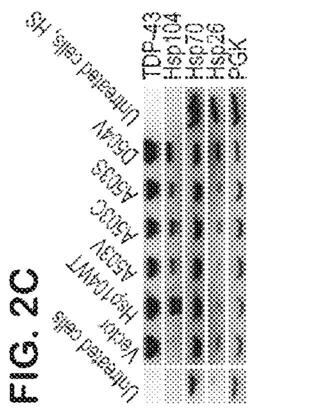
FIG. 2C
Untreated cells
Vector
Hsp104WT
A503V
A503C
A503S
D504V
Untreated cells, HS
TDP-43
Hsp104
Hsp70
Hsp26
PGK

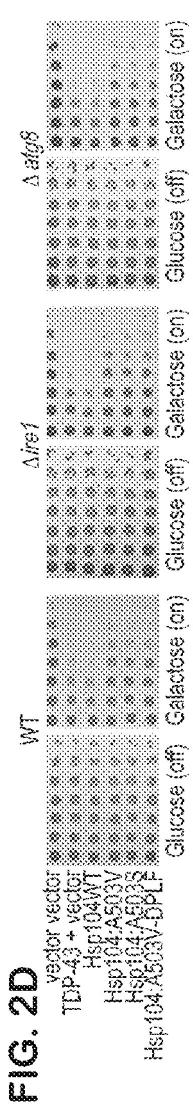
FIG. 2D
vector vector
TDP-43 + vector
Hsp104WT
Hsp104:A503V
Hsp104:A503S
Hsp104:A503V-DPLF
WT
Δire1
Δatg8
Glucose (off)
Galactose (on)

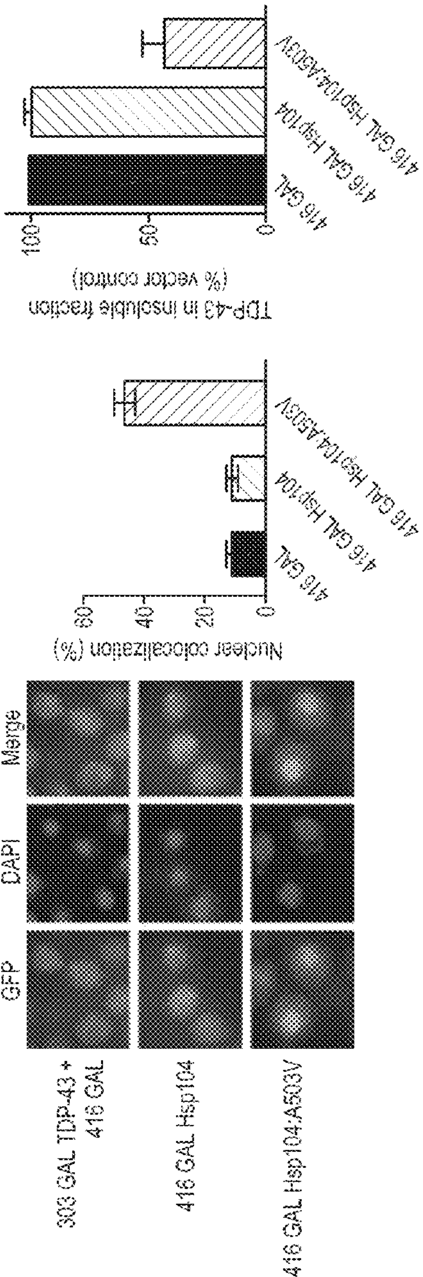
FIG. 2E
GFP
DAPI
Merge
303 GAL TDP-43 + 416 GAL
416 GAL Hsp104
416 GAL Hsp104:A503V

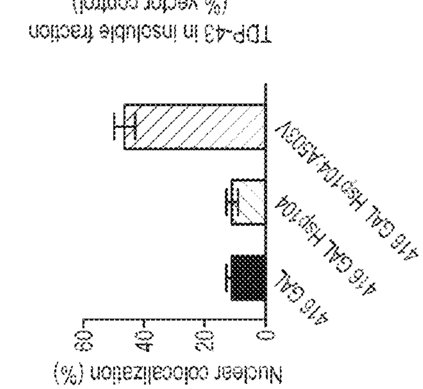
Nuclear colocalization (%)
416 GAL
416 GAL Hsp104
416 GAL Hsp104:A503V

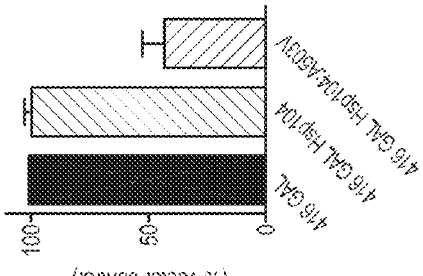
FIG. 2F
TDP-43 in insoluble fraction (% vector control)
416 GAL
416 GAL Hsp104
416 GAL Hsp104:A503V

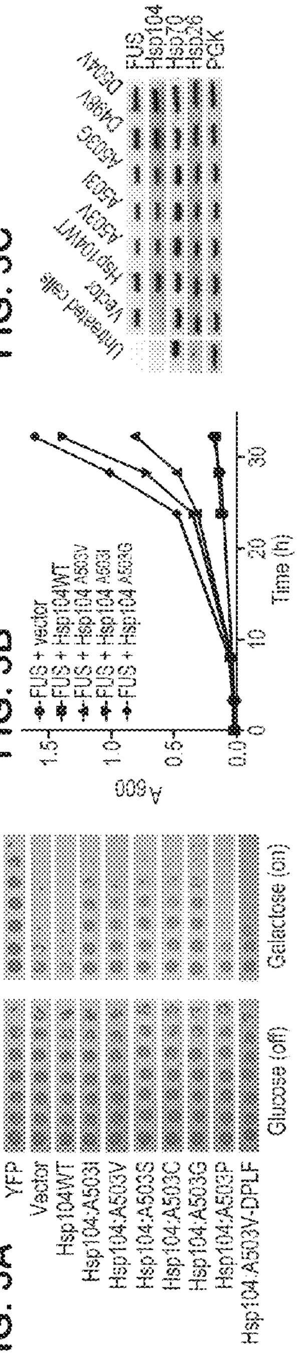
FIG. 3A
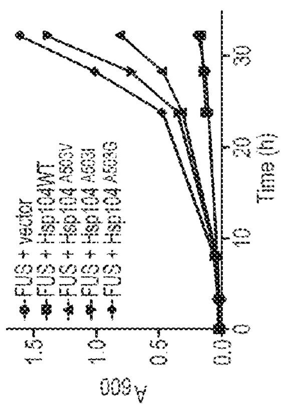
FIG. 3B
FIG. 3C
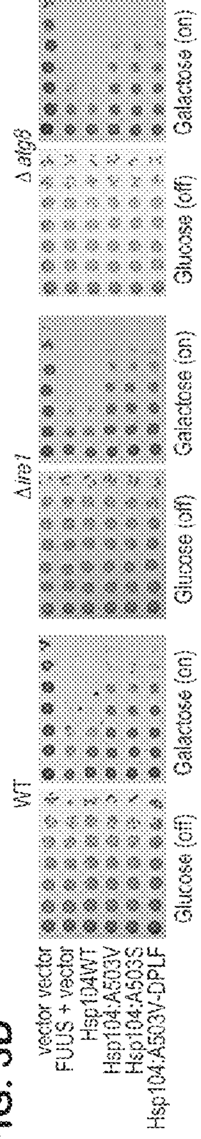
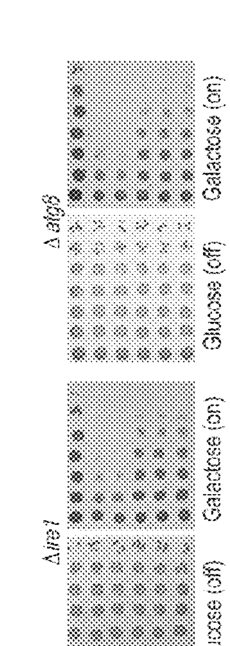
FIG. 3D
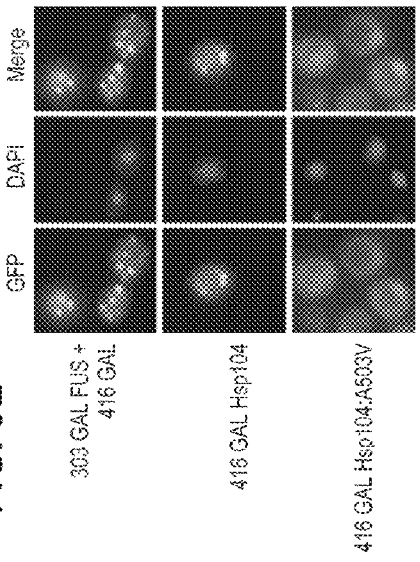
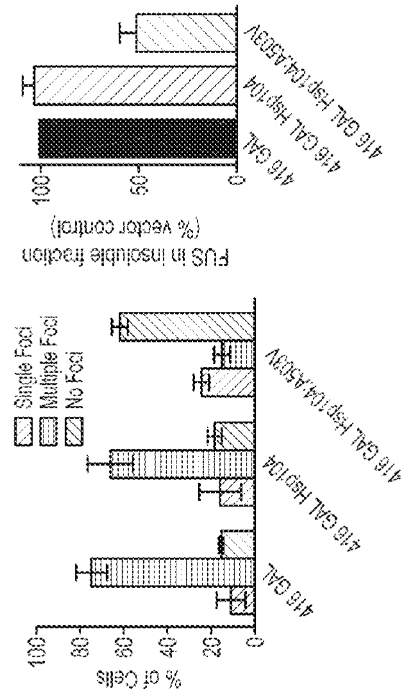
FIG. 3E
FIG. 3F

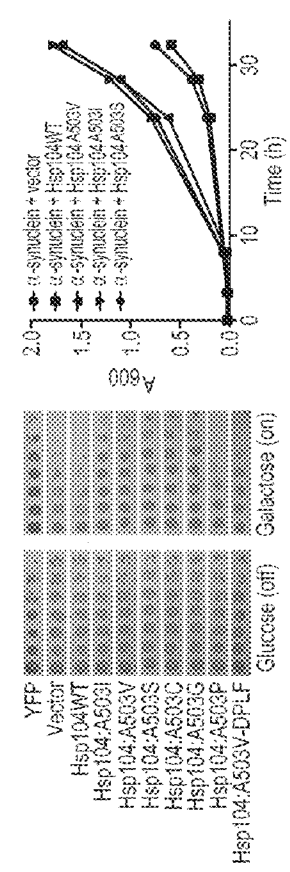
FIG. 4A
FIG. 4B
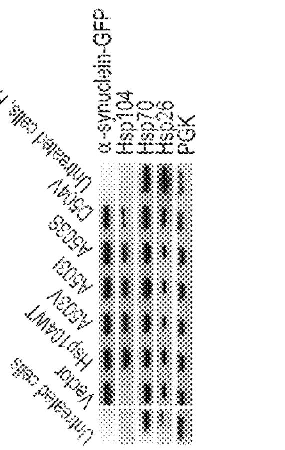
FIG. 4C
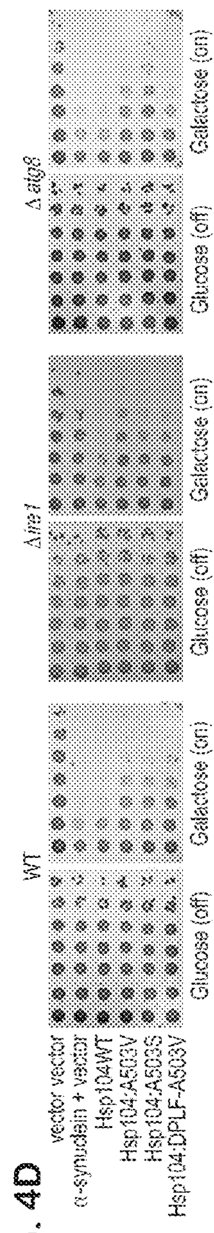
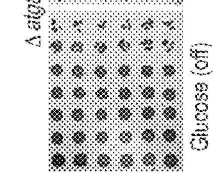
FIG. 4D
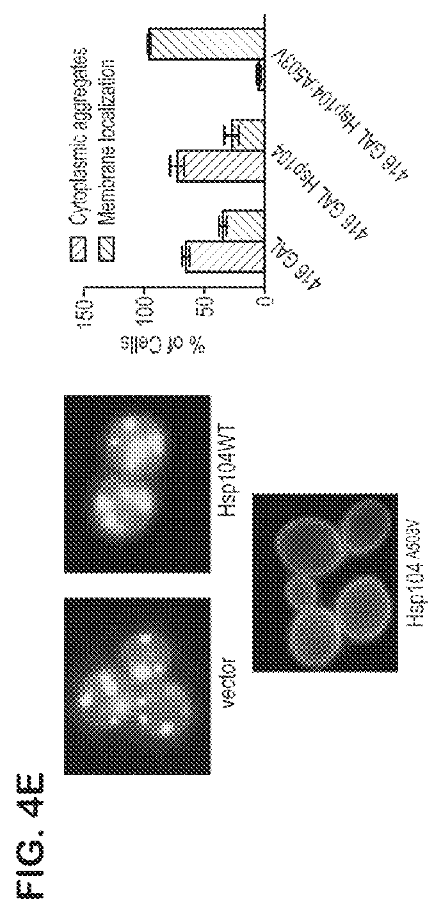
FIG. 4E
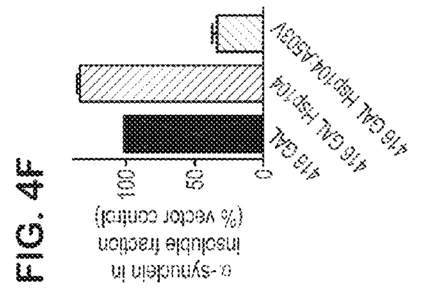
FIG. 4F

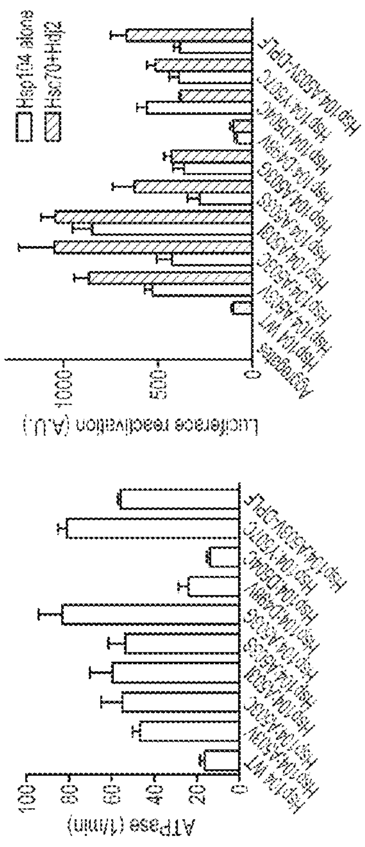
FIG. 6A
FIG. 6B
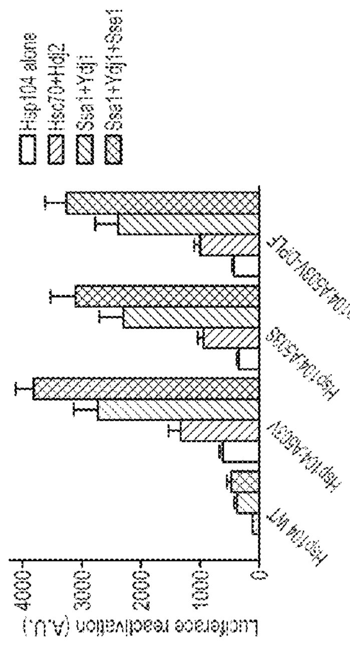
FIG. 6C
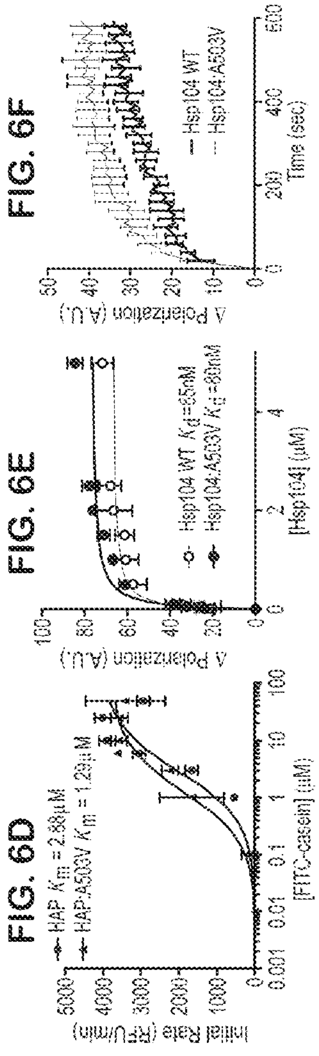
FIG. 6D
FIG. 6E
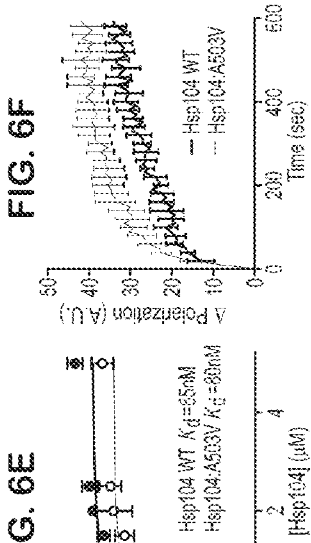
FIG. 6F
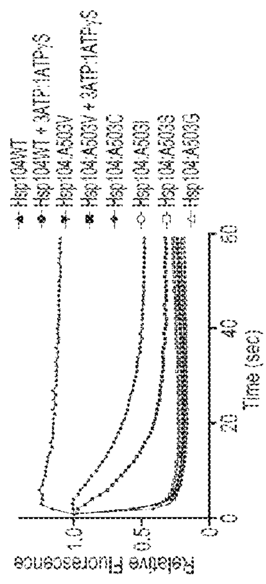
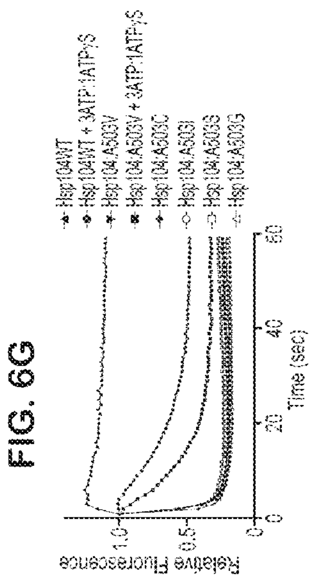
FIG. 6G
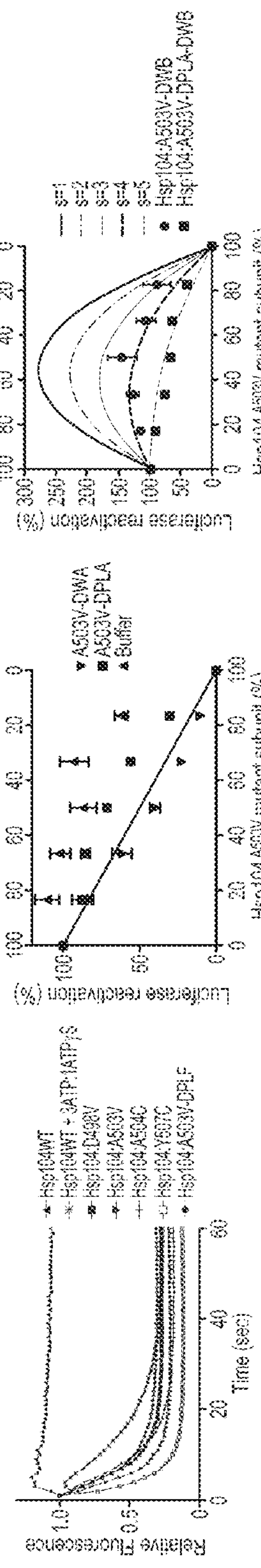
FIG. 6H
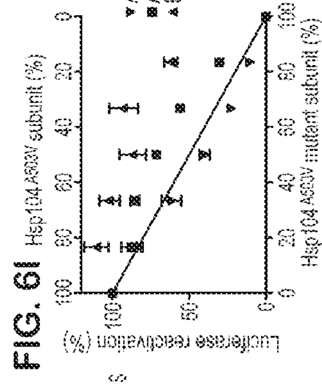
FIG. 6I
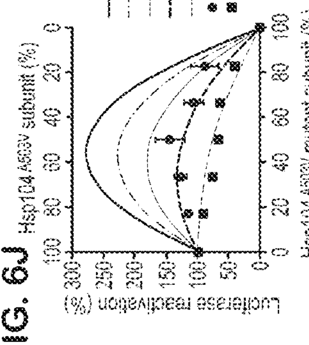
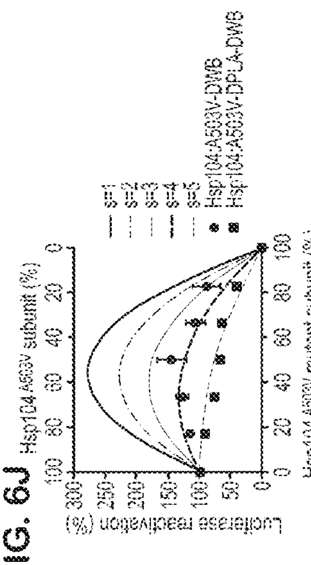
FIG. 6J

FIG. 11A

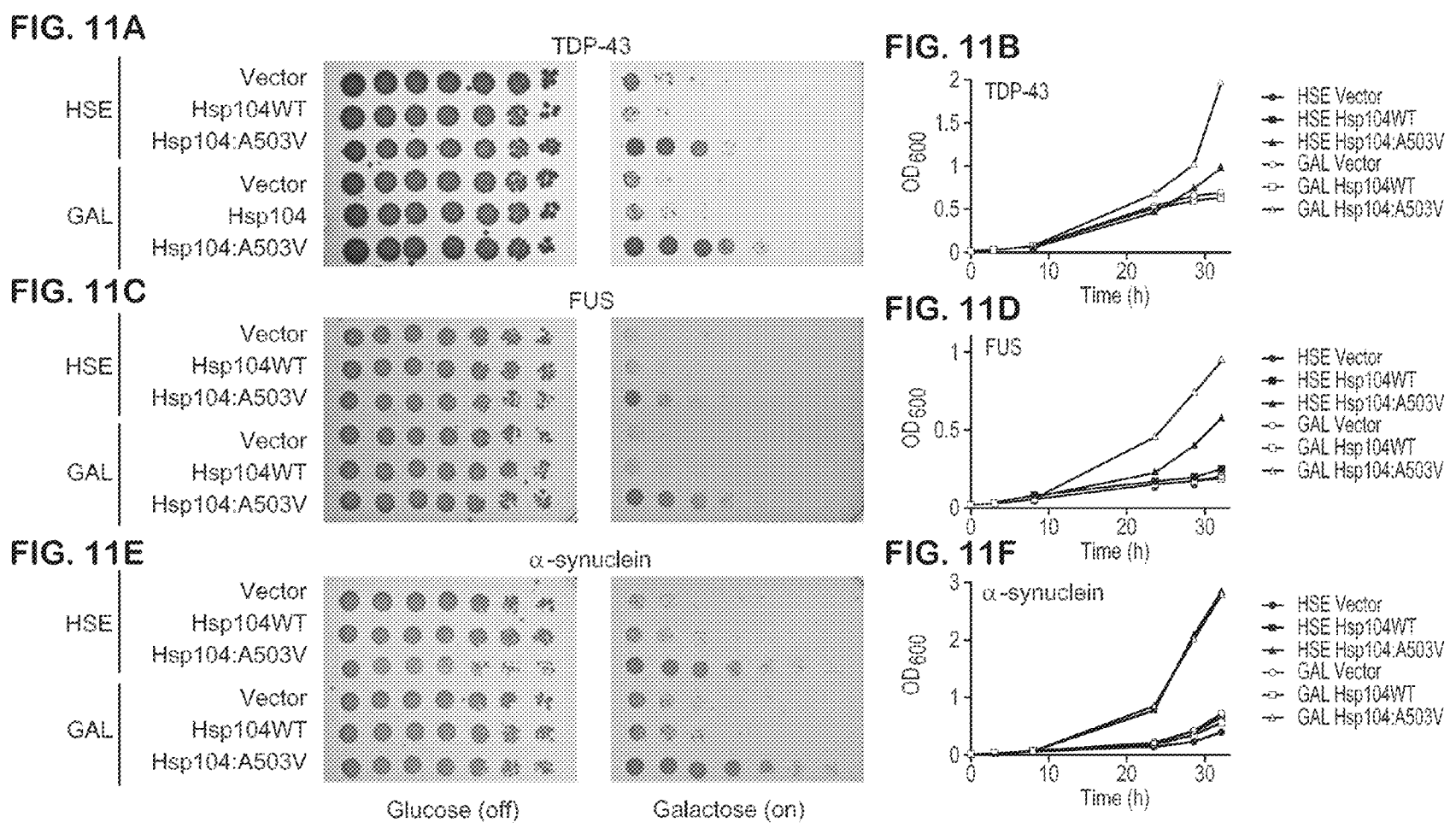

TDP-43

HSE: Vector, Hsp104WT, Hsp104:A503V
GAL: Vector, Hsp104, Hsp104:A503V

FIG. 11B

TDP-43

$OD_{600}$: 0, 0.5, 1, 1.5, 2
Time (h): 0, 10, 20, 30

HSE Vector
HSE Hsp104WT
HSE Hsp104:A503V
GAL Vector
GAL Hsp104WT
GAL Hsp104:A503V

FIG. 11C

FUS

HSE: Vector, Hsp104WT, Hsp104:A503V
GAL: Vector, Hsp104WT, Hsp104:A503V

FIG. 11D

FUS $OD_{600}$: 0, 0.5, 1
Time (h): 0, 10, 20, 30

HSE Vector
HSE Hsp104WT
HSE Hsp104:A503V
GAL Vector
GAL Hsp104WT
GAL Hsp104:A503V

FIG. 11E

α-synuclein

HSE: Vector, Hsp104WT, Hsp104:A503V
GAL: Vector, Hsp104WT, Hsp104:A503V

Glucose (off) Galactose (on)

FIG. 11F

α-synuclein $OD_{600}$: 0, 1, 2, 3
Time (h): 0, 10, 20, 30

HSE Vector
HSE Hsp104WT
HSE Hsp104:A503V
GAL Vector
GAL Hsp104WT
GAL Hsp104:A503V

SEQUENCE LISTING

```
<160> NUMBER OF SEQ ID NOS: 7

<210> SEQ ID NO 1
<211> LENGTH: 908
<212> TYPE: PRT
<213> ORGANISM: Saccharomyces cerevisiae

<400> SEQUENCE: 1

Met Asn Asp Gln Thr Gln Phe Thr Glu Arg Ala Leu Thr Ile Leu Thr
1               5                   10                  15

Leu Ala Gln Lys Leu Ala Ser Asp His Gln His Pro Gln Leu Gln Pro
            20                  25                  30

Ile His Ile Leu Ala Ala Phe Ile Glu Thr Pro Glu Asp Gly Ser Val
        35                  40                  45

Pro Tyr Leu Gln Asn Leu Ile Glu Lys Gly Arg Tyr Asp Tyr Asp Leu
    50                  55                  60

Phe Lys Lys Val Val Asn Arg Asn Leu Val Arg Ile Pro Gln Gln Gln
65                  70                  75                  80

Pro Ala Pro Ala Glu Ile Thr Pro Ser Tyr Ala Leu Gly Lys Val Leu
                85                  90                  95

Gln Asp Ala Ala Lys Ile Gln Lys Gln Gln Lys Asp Ser Phe Ile Ala
            100                 105                 110

Gln Asp His Ile Leu Phe Ala Leu Phe Asn Asp Ser Ser Ile Gln Gln
        115                 120                 125

Ile Phe Lys Glu Ala Gln Val Asp Ile Glu Ala Ile Lys Gln Gln Ala
    130                 135                 140

Leu Glu Leu Arg Gly Asn Thr Arg Ile Asp Ser Arg Gly Ala Asp Thr
145                 150                 155                 160

Asn Thr Pro Leu Glu Tyr Leu Ser Lys Tyr Ala Ile Asp Met Thr Glu
                165                 170                 175

Gln Ala Arg Gln Gly Lys Leu Asp Pro Val Ile Gly Arg Glu Glu Glu
            180                 185                 190
```

```
Ile Arg Ser Thr Ile Arg Val Leu Ala Arg Arg Ile Lys Ser Asn Pro
        195                 200                 205

Cys Leu Ile Gly Glu Pro Gly Ile Gly Lys Thr Ala Ile Ile Glu Gly
    210                 215                 220

Val Ala Gln Arg Ile Ile Asp Asp Asp Val Pro Thr Ile Leu Gln Gly
225                 230                 235                 240

Ala Lys Leu Phe Ser Leu Asp Leu Ala Ala Leu Thr Ala Gly Ala Lys
                245                 250                 255

Tyr Lys Gly Asp Phe Glu Glu Arg Phe Lys Gly Val Leu Lys Glu Ile
            260                 265                 270

Glu Glu Ser Lys Thr Leu Ile Val Leu Phe Ile Asp Glu Ile His Met
        275                 280                 285

Leu Met Gly Asn Gly Lys Asp Asp Ala Ala Asn Ile Leu Lys Pro Ala
    290                 295                 300

Leu Ser Arg Gly Gln Leu Lys Val Ile Gly Ala Thr Thr Asn Asn Glu
305                 310                 315                 320

Tyr Arg Ser Ile Val Glu Lys Asp Gly Ala Phe Glu Arg Arg Phe Gln
                325                 330                 335

Lys Ile Glu Val Ala Glu Pro Ser Val Arg Gln Thr Val Ala Ile Leu
            340                 345                 350

Arg Gly Leu Gln Pro Lys Tyr Glu Ile His His Gly Val Arg Ile Leu
        355                 360                 365

Asp Ser Ala Leu Val Thr Ala Ala Gln Leu Ala Lys Arg Tyr Leu Pro
    370                 375                 380

Tyr Arg Arg Leu Pro Asp Ser Ala Leu Asp Leu Val Asp Ile Ser Cys
385                 390                 395                 400

Ala Gly Val Ala Val Ala Arg Asp Ser Lys Pro Glu Glu Leu Asp Ser
                405                 410                 415

Lys Glu Arg Gln Leu Gln Leu Ile Gln Val Glu Ile Lys Ala Leu Glu
            420                 425                 430

Arg Asp Glu Asp Ala Asp Ser Thr Thr Lys Asp Arg Leu Lys Leu Ala
        435                 440                 445

Arg Gln Lys Glu Ala Ser Leu Gln Glu Glu Leu Glu Pro Leu Arg Gln
    450                 455                 460

Arg Tyr Asn Glu Glu Lys His Gly His Glu Glu Leu Thr Gln Ala Lys
465                 470                 475                 480

Lys Lys Leu Asp Glu Leu Glu Asn Lys Ala Leu Asp Ala Glu Arg Arg
                485                 490                 495

Tyr Asp Thr Ala Thr Ala Ala Asp Leu Arg Tyr Phe Ala Ile Pro Asp
            500                 505                 510

Ile Lys Lys Gln Ile Glu Lys Leu Glu Asp Gln Val Ala Glu Glu Glu
        515                 520                 525

Arg Arg Ala Gly Ala Asn Ser Met Ile Gln Asn Val Val Asp Ser Asp
    530                 535                 540

Thr Ile Ser Glu Thr Ala Ala Arg Leu Thr Gly Ile Pro Val Lys Lys
545                 550                 555                 560

Leu Ser Glu Ser Glu Asn Glu Lys Leu Ile His Met Glu Arg Asp Leu
                565                 570                 575

Ser Ser Glu Val Val Gly Gln Met Asp Ala Ile Lys Ala Val Ser Asn
            580                 585                 590

Ala Val Arg Leu Ser Arg Ser Gly Leu Ala Asn Pro Arg Gln Pro Ala
        595                 600                 605

Ser Phe Leu Phe Leu Gly Leu Ser Gly Ser Gly Lys Thr Glu Leu Ala
```

```
    610                 615                 620

Lys Lys Val Ala Gly Phe Leu Phe Asn Asp Glu Asp Met Met Ile Arg
625                 630                 635                 640

Val Asp Cys Ser Glu Leu Ser Glu Lys Tyr Ala Val Ser Lys Leu Leu
                645                 650                 655

Gly Thr Thr Ala Gly Tyr Val Gly Tyr Asp Glu Gly Gly Phe Leu Thr
            660                 665                 670

Asn Gln Leu Gln Tyr Lys Pro Tyr Ser Val Leu Leu Phe Asp Glu Val
        675                 680                 685

Glu Lys Ala His Pro Asp Val Leu Thr Val Met Leu Gln Met Leu Asp
    690                 695                 700

Asp Gly Arg Ile Thr Ser Gly Gln Gly Lys Thr Ile Asp Cys Ser Asn
705                 710                 715                 720

Cys Ile Val Ile Met Thr Ser Asn Leu Gly Ala Glu Phe Ile Asn Ser
                725                 730                 735

Gln Gln Gly Ser Lys Ile Gln Glu Ser Thr Lys Asn Leu Val Met Gly
            740                 745                 750

Ala Val Arg Gln His Phe Arg Pro Glu Phe Leu Asn Arg Ile Ser Ser
        755                 760                 765

Ile Val Ile Phe Asn Lys Leu Ser Arg Lys Ala Ile His Lys Ile Val
    770                 775                 780

Asp Ile Arg Leu Lys Glu Ile Glu Glu Arg Phe Glu Gln Asn Asp Lys
785                 790                 795                 800

His Tyr Lys Leu Asn Leu Thr Gln Glu Ala Lys Asp Phe Leu Ala Lys
                805                 810                 815

Tyr Gly Tyr Ser Asp Asp Met Gly Ala Arg Pro Leu Asn Arg Leu Ile
            820                 825                 830

Gln Asn Glu Ile Leu Asn Lys Leu Ala Leu Arg Ile Leu Lys Asn Glu
        835                 840                 845

Ile Lys Asp Lys Glu Thr Val Asn Val Val Leu Lys Lys Gly Lys Ser
    850                 855                 860

Arg Asp Glu Asn Val Pro Glu Glu Ala Glu Glu Cys Leu Glu Val Leu
865                 870                 875                 880

Pro Asn His Glu Ala Thr Ile Gly Ala Asp Thr Leu Gly Asp Asp Asp
                885                 890                 895

Asn Glu Asp Ser Met Glu Ile Asp Asp Asp Leu Asp
            900                 905


<210> SEQ ID NO 2
<211> LENGTH: 22
<212> TYPE: DNA
<213> ORGANISM: Artificial Sequence
<220> FEATURE:
<223> OTHER INFORMATION: cdk-5 5' primer

<400> SEQUENCE: 2

cgttgcgttg aaaagagtaa gg                                              22


<210> SEQ ID NO 3
<211> LENGTH: 21
<212> TYPE: DNA
<213> ORGANISM: Artificial Sequence
<220> FEATURE:
<223> OTHER INFORMATION: cdk-5 3' primer

<400> SEQUENCE: 3

ccggcatttg aggatctctg c                                               21
```

```
<210> SEQ ID NO 4
<211> LENGTH: 28
<212> TYPE: DNA
<213> ORGANISM: Artificial Sequence
<220> FEATURE:
<223> OTHER INFORMATION: alpha-synuclein 5'  primer

<400> SEQUENCE: 4

ggatgtattc atgaaaggac tttcaaag                                   28


<210> SEQ ID NO 5
<211> LENGTH: 21
<212> TYPE: DNA
<213> ORGANISM: Artificial Sequence
<220> FEATURE:
<223> OTHER INFORMATION: alpha-synuclein 3'  primer

<400> SEQUENCE: 5

ggcttcaggt tcgtagtctt g                                          21


<210> SEQ ID NO 6
<211> LENGTH: 24
<212> TYPE: DNA
<213> ORGANISM: Artificial Sequence
<220> FEATURE:
<223> OTHER INFORMATION: hsp104 5' primer

<400> SEQUENCE: 6

cactgctgct caattagcca agcg                                       24


<210> SEQ ID NO 7
<211> LENGTH: 26
<212> TYPE: DNA
<213> ORGANISM: Artificial Sequence
<220> FEATURE:
<223> OTHER INFORMATION: hsp104 3'  primer

<400> SEQUENCE: 7

cacgacttca gatcacgttc catatg                                     26
```

HSP104 VARIANTS AND USES THEREOF

CROSS-REFERENCE TO RELATED APPLICATIONS

This application claims the benefit under 35 USC 119(e) of U.S. Provisional Patent Application No. 61/944,193, filed Feb. 25, 2014, which application is incorporated herein in its entirety.

STATEMENT REGARDING FEDERALLY SPONSORED RESEARCH OR DEVELOPMENT

This invention was made with government support under training grant no. T32GM071339, NIH Director's New Innovator Award DP2OD002177, NRSA predoctoral fellowship F31NS079009, grant nos: R15NS075684, R21NS067354, R21HD074510, and R01GM099836, awarded by the National Institutes of Health, and under graduate research fellowship DGE-0822 and CAREER Award 0845020, awarded by the National Science Foundation. The government has certain rights in the invention.

INCORPORATION-BY-REFERENCE OF MATERIAL SUBMITTED IN ELECTRONIC FORM

The Sequence Listing material filed in electronic form herewith is hereby incorporated by reference. This file is labeled "UPN_14_7014USA.txt", was created on Feb. 24, 2015, and is 9,201 bytes (8.98 KB).

BACKGROUND OF THE INVENTION

Protein misfolding underpins several fatal neurodegenerative disorders, including amyotrophic lateral sclerosis (ALS) and Parkinson's disease (PD) (Cushman et al., 2010). In PD, α-synuclein (α-syn, α-syn, or α-synuclein) forms highly toxic prefibrillar oligomers and amyloid fibrils that accumulate in cytoplasmic Lewy bodies (Cushman et al., 2010). In ALS, TDP-43 or FUS accumulate in cytoplasmic inclusions in degenerating motor neurons (Robberecht and Philips, 2013). Unfortunately, treatments for these disorders are palliative and ineffective due to the apparent intractability of aggregated proteins. Effective therapies are urgently needed that eliminate the causative proteotoxic misfolded conformers via degradation or reactivation of the proteins to their native fold.

SUMMARY OF THE INVENTION

Provided herein are recombinant Hsp104 proteins of wild type amino acid sequence of SEQ ID NO: 1, comprising a missense mutation in a domain thereof. These include recombinant Hsp104 protein of wild type amino acid sequence of SEQ ID NO: 1, comprising missense mutations that yield a biological activity that reduces aggregation of TDP-43, FUS, or α-synuclein.

Also provided are methods for suppressing proteotoxicity in a mammal in need thereof, comprising administering a recombinant protein as described herein. Still further provided are methods for suppressing proteotoxicity in a mammal in need thereof, comprising administering a vector comprising a nucleic acid sequence encoding a recombinant protein as described herein.

Methods for solubilizing a misfolded protein comprising combining said misfolded protein with a recombinant protein described herein or a vector comprising a nucleic acid sequence encoding same are also provided. The misfolded protein may be, for example, misfolded soluble monomers, misfolded soluble oligomers, disordered aggregates, or amyloid fibrils. In a particular embodiment, the disordered aggregates are of TDP-43, FUS, or α-synuclein, or a combination thereof.

Also provided are methods of treating a neurodegenerative disease comprising administering a recombinant protein of the invention or a vector comprising a nucleic acid sequence encoding same. The neurodegenerative disease may be amyotrophic lateral sclerosis (ALS), Parkinson's disease, Alzheimer's disease, Huntington's disease, or another neurodegenerative disease. In one embodiment, the neurodegenerative disease is caused by or associated with the misfolding of a protein.

Still further provided are methods of identifying a mutated protein of HSP104 of wild type amino acid sequence of SEQ ID NO: 1 that inhibits the aggregation of a mammalian aggregate-prone protein in a yeast cell, comprising: (a) contacting a yeast cell that expresses a chimeric protein comprising a mammalian aggregate-prone protein with said mutated protein under conditions effective to allow the formation of an aggregate in the yeast cell; and (b) determining the ability of said mutated protein to inhibit the aggregation of the aggregate-prone protein in the yeast cell. Also provided are methods for the expression of a target protein in an in vitro translation system, said method comprising preparing a reaction mixture comprising a lysate, a gene coding for the target protein and a gene coding for a recombinant protein described herein, co-expressing the target protein and recombinant protein described herein, and separating the target protein from the mixture, wherein the co-expression is regulated by metered addition of the gene coding for a recombinant protein described herein or by providing a vector comprising the gene coding for a recombinant protein described herein and a regulatory sequence for regulating induction and strength of the expression.

BRIEF DESCRIPTION OF THE DRAWINGS

FIG. 1A is a homology model of the MD and a portion of the small domain of NBD1 of Hsp104. Side chains of key residues are shown as sticks. Helix one is shown on bottom left, helix 2 crosses the image, helix 3 is top-most right, with helix 4 below. Small domain of NBD1 is middle left. FIG. 1B reflects expression of Δhsp104 yeast strains integrated with galactose-inducible α-syn, FUS, or TDP-43 transformed with the indicated Hsp104 variant or vector control. Strains were serially diluted 5-fold and spotted on glucose (off) or galactose (on) media. FIG. 1C reflects expression of Hsp104 variants harboring missense mutations to valine ranging from residue D498 to Y507 expressed with α-syn, FUS, or TDP-43. FIG. 1D is a close-up of MD helix 3 from FIG. 1(A). Mutation of D498, A503, D504, or Y507 activates Hsp104. See also FIG. 8A-B.

FIG. 2A-F shows Hsp104A503X Variants Suppress TDP-43 Toxicity, Aggregation, and Mislocalization. FIG. 2A reflects expression of Δhsp104 yeast transformed with TDP-43 and Hsp104 variants, or YFP and vector, were serially diluted fivefold and spotted onto glucose (off) or galactose (on). FIG. 2B reflects selected strains from FIG. 2A induced in liquid and growth monitored by A600 nm. Curves from left (most steep) to right (most shallow) are TDP-43+ $Hsp104^{A503C}$, TDP-43+$Hsp104^{A503S}$, TDP-43+

Hsp104$^{A503C}$, TDP-43+ vector, TDP-43+Hsp104$^{WT}$. FIG. 2C reflects strains from FIG. 2B induced for 5 hr, lysed, and immunoblotted. Uninduced (untreated) and heat-shocked cells (HS) serve as controls. 3-Phosphoglycerate kinase (PGK1) serves as a loading control. FIG. 2D reflects expression of WT, Dire1, or Datg8 yeast cotransformed with vector control or TDP-43 plus vector or the indicated Hsp104 variant and serially diluted 5-fold and spotted onto glucose (off) or galactose (on). FIG. 2E shows fluorescence microscopy of cells coexpressing fluorescently tagged TDP-43 and Hsp104WT, Hsp104A503V, or vector. Cells were stained with DAPI to visualize nuclei (blue). TDP-43 localization was quantified by counting the number of cells containing colocalized nuclear staining. Values represent means±SEM (n=3). FIG. 2F reflects insoluble TDP-43 as a percentage of vector control. Δhsp104 yeast cotransformed with TDP-43 and vector or the indicated Hsp104 variant were induced with galactose for 5 hr at 30° C., lysed and processed for sedimentation analysis and quantitative immunoblot. The relative amount of insoluble TDP-43 was determined as a percentage of the vector control. Values represent means±SEM (n=2). See also FIGS. 9, 10A-C, and 11A-F.

FIG. 3A-F shows Hsp104A503X Variants Suppress FUS Toxicity and Aggregation. FIG. 3A reflects expression of Δhsp104 yeast transformed with FUS and the Hsp104 variants, or YFP and vector, serially diluted 5-fold and spotted onto glucose (off) or galactose (on). FIG. 3B shows selected strains from FIG. 3A induced in liquid, growth monitored by A600 nm. Curves from left (most steep) to right (most shallow) are FUS+Hsp104$^{A503G}$, FUS+Hsp104$^{A503I}$, FUS+ Hsp104$^{A503V}$, FUS+vector, FUS+Hsp104$^{WT}$. FIG. 3C reflects strains from FIG. 3B induced for 5 hr, lysed, and immunoblotted. FIG. 3D reflects expression of WT, Dire1, or Datg8 yeast cotransformed with vector control, or FUS plus vector, or the indicated Hsp104 variant and serially diluted 5-fold and spotted onto glucose (off) or galactose (on). FIG. 3E shows fluorescence microscopy of cells coexpressing FUS-GFP and Hsp104WT, Hsp104A503V, or vector. Cells were stained with Hoechst dye to visualize nuclei (blue). FUS aggregation was quantified by counting the number of cells containing 0, 1, or more than 1 foci. Values represent means±SEM (n=3). FIG. 3F shows the amount of insoluble FUS as a percentage of vector control. Single, Multiple, and No Foci are sub-bars for each group in order from left to right. Δhsp104 yeast cotransformed with FUS and vector or the indicated Hsp104 variant were induced with galactose for 5 hr at 30° C., lysed, and processed for sedimentation analysis and quantitative immunoblot. The relative amount of insoluble FUS was determined as a percentage of the vector control. Values represent means±SEM (n=2).

See also FIGS. 10A-C and 11A-F.

FIG. 4A-F shows Hsp104A503X Variants Suppress α-Syn Toxicity, Aggregation, and Mislocalization. FIG. 4A reflects expression of Δhsp104 yeast cotransformed with two copies of α-syn-YFP and the Hsp104 variants, or YFP and vector, serially diluted 5-fold and spotted onto glucose (off) or galactose (on). FIG. 4B shows selected strains from FIG. 4A induced in liquid, growth monitored by A600 nm. Curves from left (most steep) to right (most shallow) are α-syn+ Hsp104$^{A503I}$, α-syn+Hsp104$^{A503S}$, α-syn+Hsp104$^{A503V}$, α-syn+vector, α-syn+Hsp104$^{WT}$. FIG. 4C reflects strains from FIG. 4B induced for 8 hr in galactose, lysed, and immunoblotted. FIG. 4D reflects expression of WT, Dire1, or Datg8 yeast cotransformed with vector controls or α-syn plus vector or the indicated Hsp104 variant and were serially diluted 5-fold and spotted onto glucose (off) or galactose (on). FIG. 4E shows fluorescence microscopy of cells coexpressing α-syn-YFP and Hsp104WT, Hsp104A503V, or vector. α-Syn localization was quantified by counting the number of cells with plasma membrane fluorescence or cytoplasmic aggregates. Values represent means±SEM (n=3). Cytoplasmic aggregates and Membrane localization are sub-bars for each group in order from left to right. FIG. 4F shows the amount of insoluble α-synuclein as a percentage of vector control. Δhsp104 yeast cotransformed with α-syn and vector or the indicated Hsp104 variant were induced with galactose for 8 hr at 30° C., lysed, and processed for sedimentation analysis and quantitative immunoblot. The relative amount of insoluble α-syn was determined as a percentage of the vector control. Values represent means±SEM (n=2). See also FIGS. 10A-C and 11A-F.

Figure 5A:
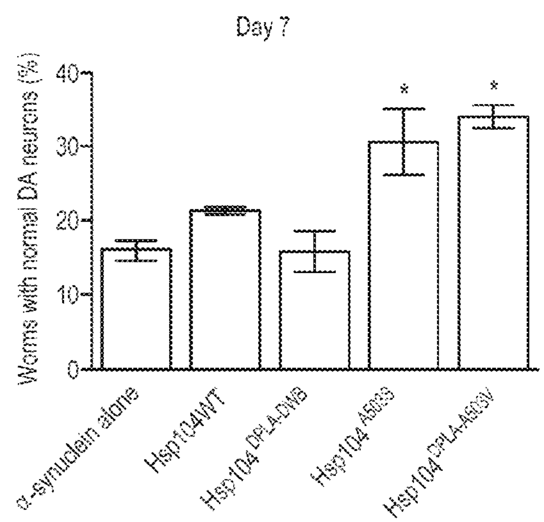
Figure 5B:
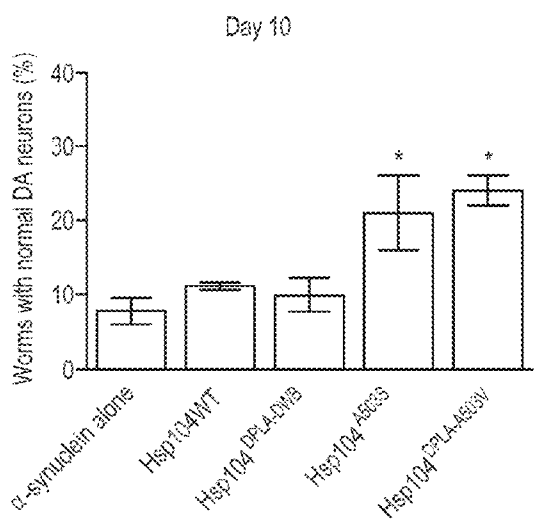
Figure 5C:
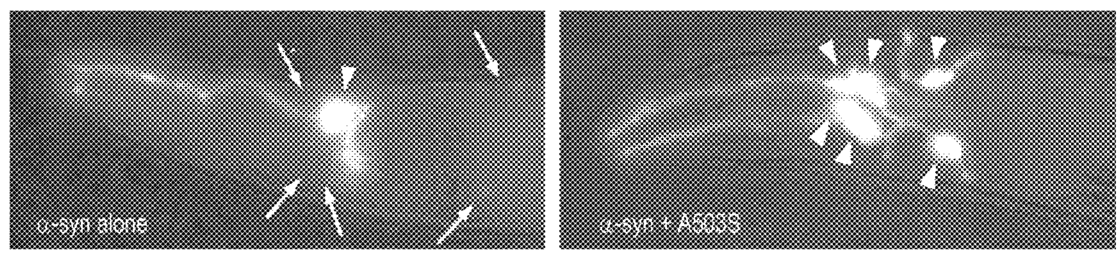

FIG. 5A-C shows that Hsp104A503S and Hsp104A503V-DPLF Protect Against α-Syn Toxicity and Dopaminergic Neurodegeneration in *C. elegans*. FIG. 5A Hsp104 variants and α-syn were coexpressed in the dopaminergic (DA) neurons of *C. elegans*. Hermaphrodite nematodes have six anterior DA neurons, which were scored at day 7 post-hatching. Hsp104A503S and Hsp104A503V-DPLF have significantly greater protective activity than both α-syn alone and the null variant. Normal worms have a full complement of DA neurons at this time. FIG. 5B At day 10, there is a decline in worms with normal DA neurons. Hsp104A503S and Hsp104A503V-DPLF exhibit greater protective activity when compared to Hsp104WT and the null variant. Values represent means±SEM (of three independent experiments, n=30 per replicate with three to four replicates per independent experiment; *p<0.05, one-way ANOVA group). Normal worms have a full complement of DA neurons at this time. FIG. 5C Photomicrographs of the anterior region of *C. elegans* coexpressing GFP with α-syn. Worms expressing α-syn alone (left) exhibit an age dependent loss of DA neurons. Worms expressing α-syn plus Hsp104A503S (right) exhibit greater neuronal integrity. Arrows indicate degenerating or missing neurons. Triangles indicate normal neurons. See also FIG. 12A-C.

FIG. 6A-J shows that potentiated Hsp104 Variants Are Tuned Differently Than Hsp104WT. FIG. 6A shows ATPase activity of Hsp104 variants. Values represent means±SEM (n=3). FIG. 6B Luciferase reactivation (as A.U.) is shown. Luciferase aggregates were incubated with Hsp104 variant plus (checkered bars) or minus (clear bars) Hsc70 (0.167 μM) and Hdj2 (0.167 μM). Values represent means±SEM (n=3). FIG. 6C Luciferase reactivation (as A.U.) is shown. Luciferase aggregates were incubated with Hsp104 variant plus or minus Hsc70 (0.167 μM) and Hdj2 (0.073 μM); Ssa1 and Ydj1; or Ssa1, Ydj1, and Sse1. Values represent means±SEM (n=3). FIG. 6D Increasing concentrations of FITC-casein were incubated with ClpP plus HAPWT or HAPA503V. Initial degradation rates were plotted against FITC-casein concentration to determine Km. Values represent means±SEM (n=3). FIG. 6E FITC-casein was incubated with increasing concentrations of Hsp104WT or Hsp104A503V. Change in fluorescence polarization was plotted against Hsp104 concentration to determine $K_d$. Values represent means±SEM (n=3). FIG. 6F Kinetics of Hsp104WT (1 μM) or Hsp104A503V (1 μM) binding to FITC-casein (0.1 μM) assessed by fluorescence polarization. Values represent means±SEM (n=3). FIGS. 6G and 6H. RepA1-70-GFP was incubated with Hsp104 variant and GroELtrap plus ATP or ATP:ATPgS (3:1). GFP unfolding was measured by fluorescence. Representative data are shown. FIG. 6I: Buffer, Hsp104A503V-DWA, or Hsp104A503V-DPLA was mixed in varying ratios with Hsp104A503V to create heterohexamer ensembles and luciferase disaggregase activity was assessed. Values represent means±SEM (n=3). Black line denotes the theoretical curve of a probabilistic mechanism where only a single A503V subunit is required for disaggregation. FIG. 6J Experiments were performed as in FIG. 6I for Hsp104A503V-DWB and Hsp104A503V-DPLA-DWB. Theoretical curves are shown wherein adjacent pairs of A503V:A503V or A503V:mutant subunits confer hexamer activity, while adjacent mutant subunits have no activity. Each adjacent A503V:A503V pair has an activity of 1/6. Adjacent A503V:mutant pairs have a stimulated activity (s), and the effect of various s values are depicted. Values represent means±SEM (n=3).

Figure 7A:
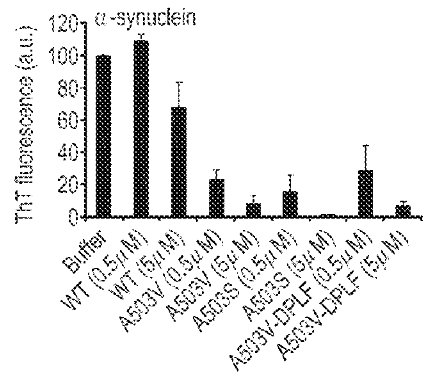
Figure 7B:
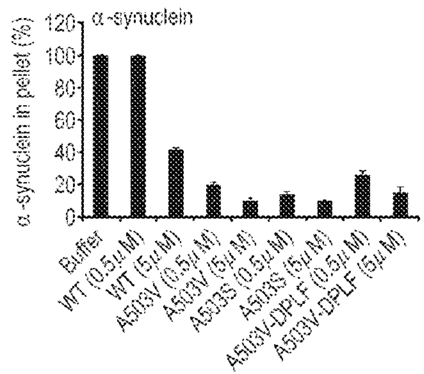
Figure 7C:
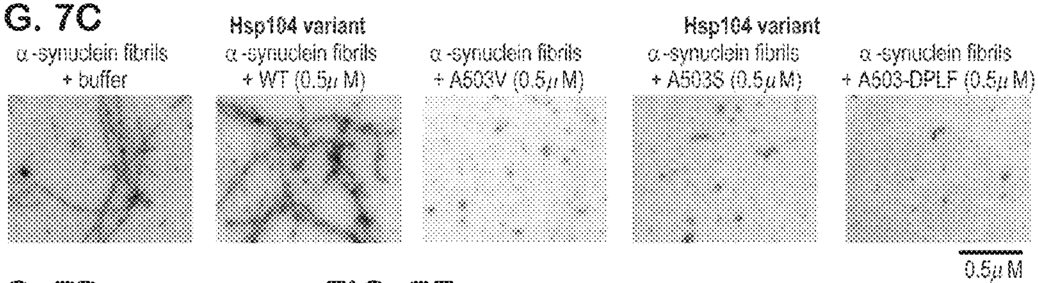

FIG. 7A-G shows potentiated Hsp104 Variants Disaggregate Preformed α-Syn, TDP-43, and FUS Fibrils More Efficaciously Than Hsp104WT. FIGS. 7A-7C. α-syn fibrils were incubated without or with Hsp104WT, Hsp104A503V, Hsp104A503S, or Hsp104A503V-DPLF for 1 hr at 30° C. Fiber disassembly was assessed by ThT fluorescence (FIG. 7A), sedimentation analysis (FIG. 7B), or (FIG. 7C) EM (bar, 0.5 mm). (FIGS. 7A and 7B—Values represent means±SEM (n=2.)) FIGS. 7D and 7E: TDP-43 aggregates were incubated with buffer, Hsp104WT, Hsp104A503V, or Hsp104A503S plus or minus Ssa1, Ydj1, and Sse1 for 1 hr at 30° C. (FIG. 7D) Aggregate dissolution assessed by turbidity. Values represent means±SEM (n=3). (FIG. 7E) Aggregate dissolution assessed by EM. Scale bar, 0.5 mm. (FIGS. 7F and 7G) FUS aggregates were incubated with buffer, Hsp104WT, Hsp104A503V, or Hsp104A503S plus or minus Ssa1, Ydj1, and Sse1 for 1 hr at 30° C. (FIG. 7F) Aggregate dissolution assessed by turbidity (absorbance at 395 nm). Values represent means±SEM (n=3). (FIG. 7G) Aggregate dissolution assessed by EM. Scale bar, 0.5 mm.

Figure 8A:
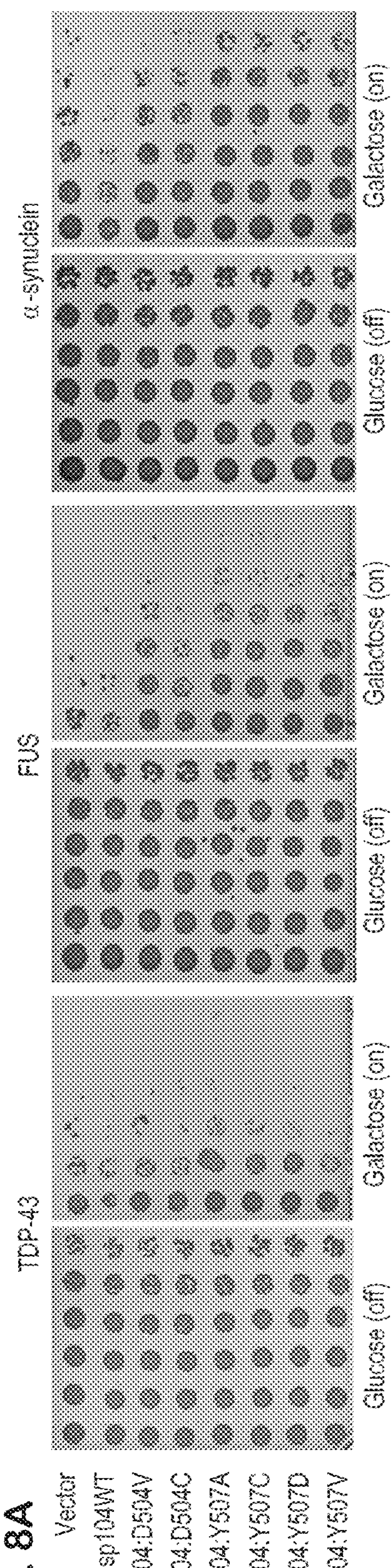
Figure 8B:
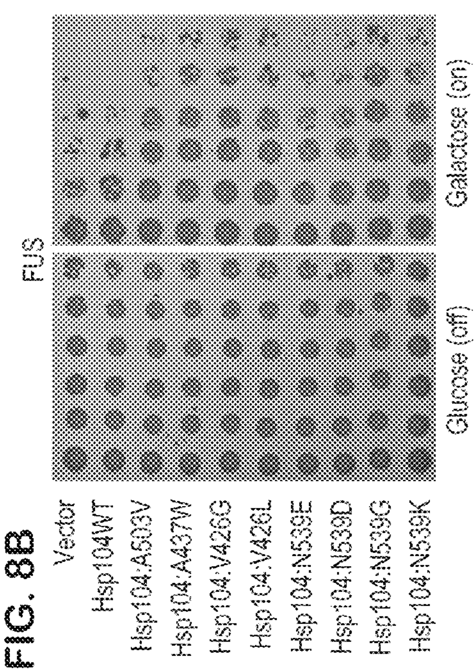

FIG. 8A-B reflects specific Hsp104 MD Variants Suppress Toxicity of TDP-43, FUS, and α-synuclein in Yeast, Related to FIG. 1. FIG. 8A Residues D504 and Y507 were mutated to the indicated residues and compared to the Hsp104WT for the ability to suppress TDP-43 (left), FUS (center), or α-synuclein (right) toxicity in Dhsp104 yeast. At both positions, various mutations suppress toxicity. FIG. 8B: Additional variants were constructed at residues V426 and N539 and compared to the Hsp104WT for the ability to suppress FUS toxicity in yeast.

Figure 9:
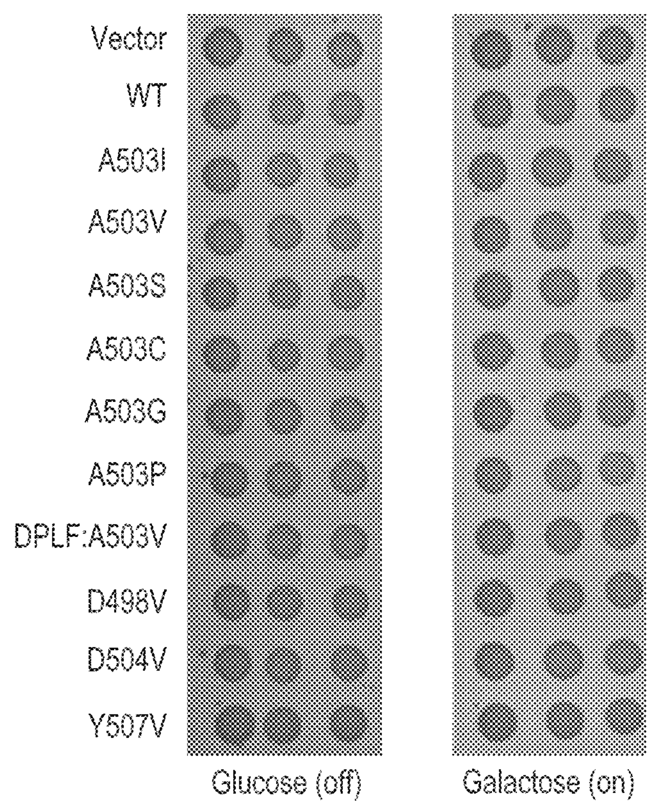

FIG. 9 reflects that potentiated Hsp104 Variants Are Not Overtly Toxic to Yeast at 30° C., Related to FIG. 2A-F. The variants were assessed for toxicity by expressing the variants in the 416 GAL vector in Dhsp104 yeast at 30° C.

Figure 10A:
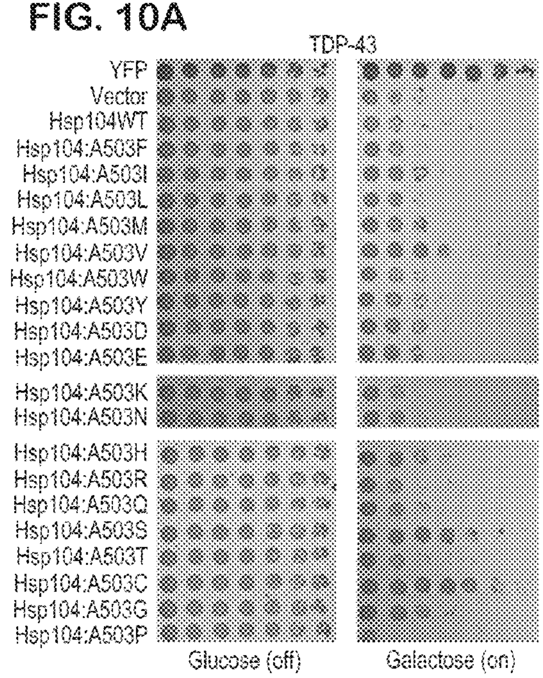
Figure 10B:
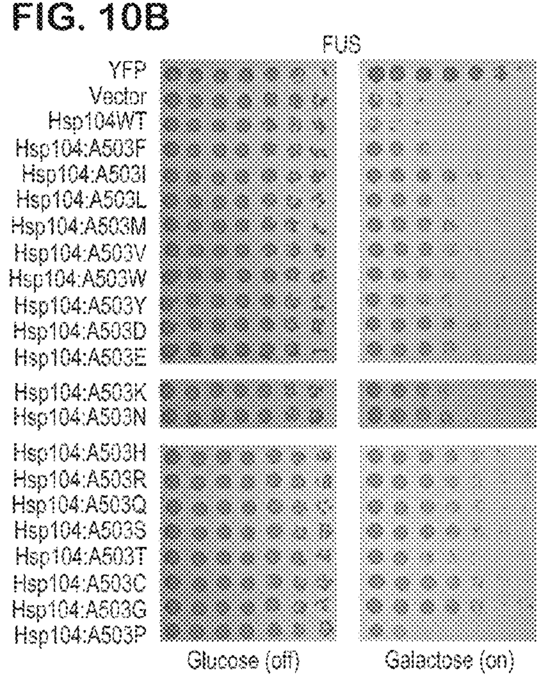
Figure 10C:
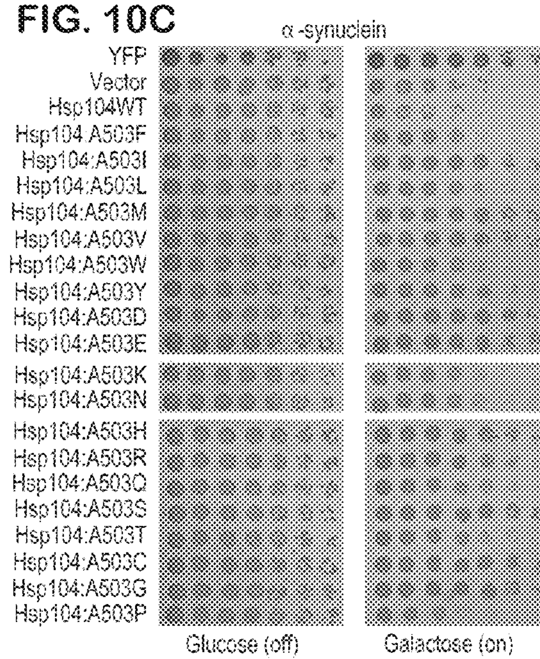

FIG. 10A-C demonstrates that Mutation of Residue A503 to Almost Any Amino Acid Reveals a Therapeutic Gain-of-Function Phenotype, Related to FIGS. 2A-F, 3A-F, and 4A-F. A503 of Hsp104 was mutated to all amino acids and co-expressed with TDP-43 (FIG. 10A), FUS (FIG. 10B), and α-synuclein (FIG. 10C) in Δhsp104 yeast. Mutation to any amino acid with the exception of proline suppresses toxicity.

FIG. 11A-F reflects expression of Hsp104A503V from the Endogenous HSP104 Promoter or Galactose Promoter Rescues TDP-43, FUS, or α-synuclein Toxicity in Yeast, Related to FIGS. 2A-F, 3A-F, and 4A-F. TDP-43 (FIGS. 11A and 11B), FUS (FIGS. 11C and 11D), or α-synuclein (FIGS. 11E and F) were expressed from the galactose-inducible promoter in Δhsp104 yeast. Hsp104A503V or Hsp104WT were co-expressed from Hsp104's native promoter or the galactose-inducible promoter. Empty vector serves as a negative control. Expression from Hsp104's native promoter yields lower expression levels than the galactose-inducible promoter under basal conditions. Toxicity was assessed by spotting assay (FIGS. 11A, 11C, 11E) or by growth in liquid culture (FIGS. 11B, 11D, 11F). Lower levels of Hsp104A503V expression from the endogenous HSP104 promoter still suppress toxicity in each model.

Figure 12A:
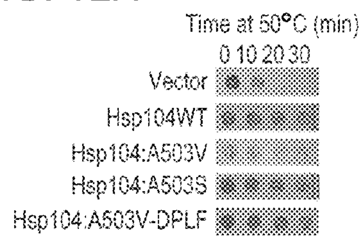
Figure 12B:
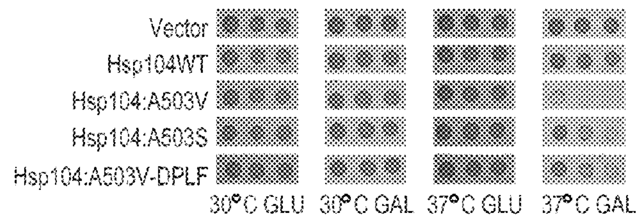
Figure 12C:
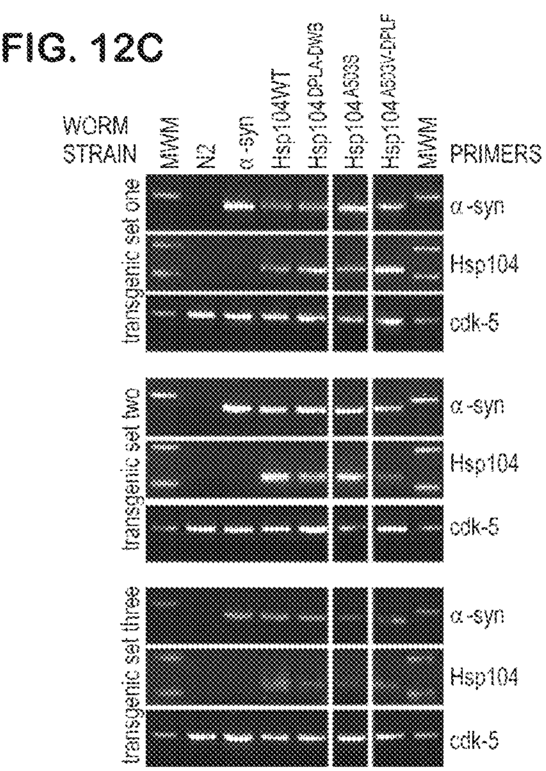

FIG. 12A-C shows properties of Hsp104A503S and Hsp104A503V-DPLF, Related to FIG. 5A-C. FIG. 12A: W303aΔhsp104 yeast were transformed with the indicated 416GAL-Hsp104 plasmid (Hsp104WT, Hsp104A503V, Hsp104A503S or Hsp104A503V-DPLF) or empty vector control. Yeast were grown to saturation in synthetic raffinose media and then diluted to A600 nm=0.3 in galactose supplemented media. After 4 h growth at 30° C., cells were heat shocked at 50° C. for 0-30 min and then cooled for 2 min on ice. Cultures were serially diluted and spotted on synthetic dropout media supplemented with galactose and the plates were incubated at 30° C. for 2-3 days. FIG. 12B: W303aDhsp104 yeast were transformed with the indicated 416GAL-Hsp104 plasmid (Hsp104WT, Hsp104A503V, Hsp104A503S and Hsp104A503V-DPLF) or empty vector control. Yeast were diluted and grown in synthetic raffinose medium overnight. Cultures were grown in synthetic raffinose medium to A600 nm=2.0 and spotted onto SD-Ura or SGa1-Ura media and incubated at 30° C. or 37° C. Plates were analyzed after 2-3 days of growth. FIG. 12C: Semi-quantitative RT-PCR confirms transcription of HSP104 variants. The transcription of α-synuclein, each HSP104 construct, and a neuronal housekeeping gene cdk-5 were assessed by semiquantitative RT-PCR using primer pairs described in the Experimental Procedures. HSP104 lines have variable expression levels, as each independent line will have a different copy number of the expressed transgene. Based on these results, α-synuclein does not appear to be regulated at the transcriptional level by any HSP104 variant, which suggests that any protection observed is most likely at the translational or post-translational level.

DETAILED DESCRIPTION OF THE INVENTION

There are no therapies that reverse the proteotoxic misfolding events that underpin fatal neurodegenerative diseases, including amyotrophic lateral sclerosis (ALS) and Parkinson's disease (PD). Hsp104, a conserved hexameric AAA+ protein from yeast, solubilizes disordered aggregates and amyloid but has no metazoan homolog and only limited activity against human neurodegenerative disease proteins. Here, we reprogram Hsp104 to rescue TDP-43, FUS, and α-synuclein proteotoxicity by mutating single residues in helix 1, 2, or 3 of the middle domain or the small domain of nucleotide-binding domain 1.

Potentiated Hsp104 variants enhance aggregate dissolution, restore proper protein localization, sup-press proteotoxicity, and in a *C. elegans* PD model attenuate dopaminergic neurodegeneration. Potentiating mutations reconfigure how Hsp104 subunits collaborate, desensitize Hsp104 to inhibition, obviate any requirement for Hsp70, and enhance ATPase, translocation, and unfoldase activity. Our work establishes that disease-associated aggregates and amyloid are tractable targets and that enhanced disaggregases can restore proteostasis and mitigate neurodegeneration.

Inspiration can be drawn from nature, where amyloidogenesis and protein misfolding have been subjugated for adaptive modalities (Newby and Lindquist, 2013). For example, beneficial yeast prions are tightly regulated by Hsp104, a hexameric AAA+ protein that rapidly deconstructs various amyloids and prefibrillar oligomers (DeSantis et al., 2012; Lo Bianco et al., 2008; Newby and Lindquist, 2013). Hsp104 also reactivates proteins from disordered aggregates after environmental stress (Shorter, 2008). Hsp104 is highly conserved in eubacteria and eukaryotes, except in metazoa, which bafflingly lack an Hsp104 homolog and display limited ability to disaggregate disordered and amyloid aggregates (Duennwald et al., 2012; Shorter, 2008, 2011). Thus, Hsp104 could be harnessed to augment human proteostasis and counter protein misfolding in neurodegenerative disease (Shorter, 2008). Indeed, Hsp104 synergizes with human Hsp70 and Hsp40 to resolve various misfolded species linked with human neurodegenerative disease and can partially antagonize protein misfolding and neurodegeneration in metazoa (Cush-man-Nick et al., 2013; DeSantis et al., 2012; Duennwald et al., 2012; Lo Bianco et al., 2008; Shorter, 2011; Vacher et al., 2005). Hsp70 overexpression can also mitigate neurodegeneration (Cushman-Nick et al., 2013). However, these potentially therapeutic activities remain limited and vast improvements are needed to maximize therapeutic potential. Indeed, very high concentrations of Hsp104 are needed to antagonize human neurodegenerative disease proteins, which Hsp104 never ordinarily encounters, and some substrates are refractory to Hsp104 (DeSantis et al., 2012; Lo Bianco et al., 2008).

A key but elusive goal is to engineer or evolve optimized chaperones against neurodegenerative disease substrates to maximize therapeutic efficacy (Shorter, 2008). Chaperones are impractical targets for protein engineering due to their typically large size, and protein disaggregases such as Hsp104 have poorly understood structures, making rational design challenging (Saibil, 2013). Here, potentiated Hsp104 variants that eradicate TDP-43, FUS, and α-syn aggregates and potently suppress toxicity are identified. Several artificially engineered chaperones to optimize proteostasis and thwart neurodegeneration are disclosed. Herein, it is demonstrated that neuroprotection is accomplished for diverse neurodegenerative diseases via subtle structural modifications of existing chaperones.

Here, we demonstrate that Hsp104, a protein disaggregase from yeast, can be modified to powerfully eradicate diverse substrates implicated in ALS and PD. We have developed the first (to our knowledge) disaggregases (or even chaperones) engineered to optimize proteostasis. Indeed, enhanced Hsp104 variants are the first agents defined to reverse TDP-43 and FUS aggregation. They not only suppress toxicity and eliminate protein aggregates but also restore proper protein localization. Importantly, these Hsp104 variants are not overtly toxic like other MD mutants (Lipinska et al., 2013). Thus, potentiated Hsp104 variants can be uncovered that are not invariably toxic and that rescue various toxic neurodegenerative disease proteins in vitro and in vivo under conditions where Hsp104WT is impotent. Potentiated Hsp104 variants suppress neurodegeneration in a *C. elegans* PD model. Thus, we provide a promising example of engineered disaggregases rescuing neurodegeneration in a metazoan nervous system under conditions where the WT disaggregase is ineffective. Our findings suggest that general neuroprotection via activated protein disaggregases may be possible for diverse neurodegenerative diseases.

We have identified the MD as a key region governing Hsp104 function. It is surprising and unprecedented that missense mutations to nearly any residue at specific and disparate positions (e.g., A503, Y507) confer a therapeutic gain of function. Potentiation stems from loss of amino acid identity rather than specific mutation. Thus, Hsp104 activity is likely tightly constrained but can be unleashed by subtle changes to side chains at specific positions. These constraints are too tight for Hsp104WT to counter TDP-43, FUS, and α-syn aggregation and toxicity under the conditions employed in our experiments. Thus, we reveal a surprising inimical deficit in existing disaggregase functionality. MD functions as a capacitor braced to un-leash Hsp104 activity. Missense mutations at specific positions in MD helix 1, 2, or 3 or the small domain of NBD1 (immediately C terminal to the MD) likely destabilize autoinhibitory interactions that dampen Hsp104 activity or induce conformational changes that mimic or aid in an allosteric activation step. Potentiating mutations obviate any absolute requirement for Hsp70 and enhance Hsp104 ATPase activity, substrate translocation speed, unfoldase activity, and amyloid disaggregase activity. Additionally, Hsp104A503V hexamers display enhanced plasticity and are more resistant to defective subunits than Hsp104WT. Thus, enhanced variants possess a more robust disaggregase activity that is desensitized to inhibition. Irrespective of the mechanism of activation, we have established that seemingly minor structural modulation of a disaggregase can suppress a constellation of otherwise intractable proteotoxicities in vivo. We are unaware of any precedent for attaining such a wide-reaching set of gain of therapeutic functions via such minor changes in primary sequence, e.g., by removing a single methyl group (A503G) or by adding a single methylene bridge (V426L).

Enhanced variants that specifically target single proteins (e.g., disaggregate FUS, but not TDP-43) are valuable to minimize any off-target effects. Hsp104 can be potentiated against any protein, which might find key applications in purification of troublesome recombinant proteins. Modified/mutated Hsp104 is useful as a therapeutic. Protein aggregates are not intractable and general neuroprotection via altered proteostasis is achievable. In some embodiments, potentiated Hsp104 variants are introduced in short transient bursts to restore natural proteostasis. In this way, long-term expression of an exogenous protein is avoided. However, long-term expression is also provided for where advantageous in the management of chronic disorders. Reactivation of disease-associated proteins to their nonpathogenic states provides for the halting and/or reversing of neurodegenerative disease.

A Hsp104 protein or mutant/variant thereof as described herein is a monomer. Each wild-type Hsp104 monomer contains two nucleotide-binding domains (NBD1 and NBD2) as well as an N-terminal, middle, and C-terminal domain (DeSantis and Shorter, 2012). Wild-type Hsp104 forms ring-shaped hexamers with a central pore through which substrate is threaded.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization are those well-known and commonly employed in the art.

Standard techniques are used for nucleic acid and peptide synthesis. The techniques and procedures are generally performed according to conventional methods in the art and various general references (e.g., Sambrook and Russell, 2001, Molecular Cloning, A Laboratory Approach, Cold Spring Harbor Press, Cold Spring Harbor, N.Y., and Ausubel et al., 2002, Current Protocols in Molecular Biology, John Wiley & Sons, NY), which are provided throughout this document. The nomenclature used herein and the laboratory procedures used in analytical chemistry and organic syntheses described below are those well-known and commonly employed in the art. Standard techniques or modifications thereof, are used for chemical syntheses and chemical analyses.

As used herein, each of the following terms has the meaning associated with it in this section.

By "amino acid", both naturally occurring and synthetic amino acids are contemplated. Conservative amino acids are intended to be those sharing a common property recognized by one of skill in the art. In one embodiment, common properties are, e.g., amino acids having hydrophobic non-acidic side chains, amino acids having hydrophobic acidic side chains, amino acids having hydrophilic nonacidic side chains, amino acids having hydrophilic acidic side chains, and amino acids having hydrophilic basic side chains. The term also includes other amino acids found in nature, including metabolic intermediates. For example, selenocystein and hydroxyproline are contemplated amino acids. In another embodiment, common properties are, e.g., amino acids having hydrophobic side chains, amino acids having aliphatic hydrophobic side chains, amino acids having aromatic hydrophobic side chains, amino acids with polar neutral side chains, amino acids with electrically charged side chains, amino acids with electrically charged acidic side chains, and amino acids with electrically charged basic side chains. In another embodiment, the amino acids are all those lacking a pyrrolidine ring. In another embodiment, the amino acids are all those lacking a saturated heterocycle.

As used throughout this specification and the claims, the terms "comprising" and "including" are inclusive of other components, elements, integers, steps and the like. Conversely, the term "consisting" and its variants are exclusive of other components, elements, integers, steps and the like.

A "disease" is a state of health of subject wherein the subject cannot maintain homeostasis, and wherein if the disease is not ameliorated then the subject's health continues to deteriorate. In contrast, a "disorder" in an subject is a state of health in which the subject is able to maintain homeostasis, but in which the subject's state of health is less favorable than it would be in the absence of the disorder. Left untreated, a disorder does not necessarily cause a further decrease in the subject's state of health. In preferred embodiments, the subject is an animal. In more preferred embodiments, the subject is a mammal. In most preferred embodiments, the subject is a human. The term "condition" is used herein to refer to a disease and/or a disorder, as apparent to one of skill in the art in context.

A disease or disorder is "alleviated" or "palliated" if the severity of a cause or symptom of the disease or disorder, or the frequency with which such a cause or symptom is experienced in a subject, or both, are reduced. A disease or disorder is "inhibited" if one or more causes or symptoms is reduced such as to not be experienced by the subject. A disease or disorder is "prevented" if one or more causes or symptoms are stopped from occurring or recurring as a result of one-time, periodic, or continuous treatment.

The terms "a-syn", "α-syn", "a-synuclein", and "α-synuclein" are used interchangeably throughout to refer to the alpha-synuclein protein.

The terms "effective amount" and "pharmaceutically effective amount" refer to a nontoxic but sufficient amount of an agent to provide the desired biological result. That result can be reduction and/or alleviation of the signs, symptoms, or causes of a disease or disorder, or any other desired alteration of a biological system. An appropriate effective amount in any individual case may be determined by one of ordinary skill in the art using routine experimentation.

The term "expression" as used herein is defined as the transcription and/or translation of a particular nucleotide sequence.

The term "FUS" refers to an RNA-binding protein (Fused in Sarcoma).

The terms "mutation" and "missense mutation" are used interchangeably throughout unless otherwise apparent from context, and refer to one or more amino acid alterations or nucleotide alterations that cause expression of peptides having one or more amino acid alterations. Substitutions may be conservative or non-conservative. The mutation may be of one or more nucleotides or amino acids, and may include altered nucleotide or amino acids, natural or synthetic, as known in the art. The terms mutation or missense mutation also include deletions.

The terms "mutant", "variant", are used interchangeably to refer to non-wild-type nucleotide or amino acid sequences, especially Hsp104 nucleotide or amino acid sequences, having mutations or missense mutations.

By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil). The term "nucleic acid" typically refers to large polynucleotides.

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

By "expression cassette" is meant a nucleic acid molecule comprising a coding sequence operably linked to promoter/regulatory sequences necessary for transcription and, optionally, translation of the coding sequence.

"Fragment", when used to describe a nucleotide sequence is meant to comprise or consist of 5, 10, 20, 25, 30, 35, 40, 45, 50, 55, 60, 65, 70, 75, 80, 85, 90, 95, 100, . . . 1800 contiguous nucleotides. When used to describe a polypeptide sequence, the polypeptide comprises or consists of 5, 10, 20, 25, 30, 35, 40, 45, 50, 55, 60, 65, 70, 75, 80, 85, 90, 95, 100, . . . 905 amino acids. Fragment may also include regions of a protein, particularly a Hsp104 protein, e.g., a pore loop, a nucleotide-binding domain (NBD), NBD1, NBD2, the N-terminal domain, the middle domain, the C-terminal domain, the distal loop between helix 1 and helix 2, helix 1, helix 2, helix 3. The term fragment may also include biologically active portions of the above domains.

"Identity" or "similarity" with respect to a sequence is defined herein as the percentage of amino acid residues in the candidate sequence that are identical (i.e., same residue) or similar (i.e., amino acid residue from the same group based on common side-chain properties, see below) with the peptide and polypeptide regions provided herein, after aligning the sequences and introducing gaps, if necessary, to achieve the maximum percent sequence identity. Percent (%) identity is a measure of the relationship between two polynucleotides or two polypeptides, as determined by comparing their nucleotide or amino acid sequences, respectively. In general, the two sequences to be compared are aligned to give a maximum correlation between the sequences. The alignment of the two sequences is examined and the number of positions giving an exact amino acid or nucleotide correspondence between the two sequences determined, divided by the total length of the alignment and multiplied by 100 to give a % identity figure. This % identity figure may be determined over the whole length of the sequences to be compared, which is particularly suitable for sequences of the same or very similar length and which are highly homologous, or over shorter defined lengths, which is more suitable for sequences of unequal length or which have a lower level of homology. There are a number of algorithms, and computer programs based thereon, which are available to be used the literature and/or publically or commercially available for performing alignments and percent identity. The selection of the algorithm or program is not a limitation of the present invention.

Examples of suitable alignment programs including, e.g., the software CLUSTALW under Unix and then be imported into the Bioedit program (Hall, T. A. 1999, BioEdit: a user-friendly biological sequence alignment editor and analysis program for Windows 95/98/NT. Nucl. Acids. Symp. Ser. 41:95-98); the Wisconsin Sequence Analysis Package, version 9.1 (Devereux J. et al., Nucleic Acids Res., 12:387-395, 1984, available from Genetics Computer Group, Madison, Wis., USA). The programs BESTFIT and GAP, may be used to determine the % identity between two polynucleotides and the % identity between two polypeptide sequences.

Other programs for determining identity and/or similarity between sequences include, e.g, the BLAST family of programs available from the National Center for Biotechnology Information (NCB), Bethesda, Md., USA and accessible through the home page of the NCBI, the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used; and FASTA, available as part of the Wisconsin Sequence Analysis Package). SeqWeb Software (a web-based interface to the GCG Wisconsin Package: Gap program).

An “inducible” promoter is a nucleotide sequence which, when operably linked with a polynucleotide which encodes or specifies a gene product, causes the gene product to be produced substantially only when an inducer which corresponds to the promoter is present.

“Polypeptide” refers to a polymer composed of amino acid residues, related naturally occurring structural variants, and synthetic non-naturally occurring analogs thereof linked via peptide bonds. Synthetic polypeptides can be synthesized, for example, using an automated polypeptide synthesizer.

As used herein, the term “promoter/regulatory sequence” means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a n inducible manner.

The term “protein” typically refers to large polypeptides.

The term “peptide” typically refers to short polypeptides.

Conventional notation is used herein to portray polypeptide sequences: the left-hand end of a polypeptide sequence is the amino-terminus; the right-hand end of a polypeptide sequence is the carboxyl-terminus.

A “polynucleotide” means a single strand or parallel and anti-parallel strands of a nucleic acid. Thus, a polynucleotide may be either a single-stranded or a double-stranded nucleic acid. In the context of the present invention, the following abbreviations for the commonly occurring nucleic acid bases are used. “A” refers to adenosine, “C” refers to cytidine, “G” refers to guanosine, “T” refers to thymidine, and “U” refers to uridine.

The term “oligonucleotide” typically refers to short polynucleotides, generally no greater than about 60 nucleotides. It will be understood that when a nucleotide sequence is represented by a DNA sequence (i.e., A, T, G, C), this also includes an RNA sequence (i.e., A, U, G, C) in which “U” replaces “T.”

As used herein the term “pharmaceutically acceptable carrier” is intended to include any and all solvents, dispersion media, coatings, antibacterial and antifungal agents, isotonic and absorption delaying agents, and the like, compatible with pharmaceutical administration.

The term “recombinant DNA” as used herein is defined as DNA produced by joining pieces of DNA from different sources.

The term “recombinant polypeptide” as used herein is defined as a polypeptide produced by using recombinant DNA methods.

As used herein the terms “suppress” or “suppressing” mean reducing, eliminating, or preventing.

“TDP-43” refers to TAR DNA-binding protein 43 (a.k.a. transactive response DNA binding protein 43 kDa).

The term “treatment,” as used herein, refers to reversing, alleviating, delaying the onset of, inhibiting the progress of, and/or preventing a disease or disorder, or one or more symptoms thereof, to which the term is applied in a subject. In some embodiments, treatment may be applied after one or more symptoms have developed. In other embodiments, treatment may be administered in the absence of symptoms. For example, treatment may be administered prior to symptoms (e.g., in light of a history of symptoms and/or one or more other susceptibility factors), or after symptoms have resolved, for example to prevent or delay their reoccurrence.

The wild-type sequence for Hsp104 referenced herein is SEQ ID NO: 1 as follows. It is intended that in some embodiments, natural-occurring variants hereof are encompassed by reference to the wild-type sequence (SEQ ID NO: 1).

```
[SEQ ID NO: 1:]
  1   MNDQTQFTER ALTILTLAQK LASDHQHPQL QPIHILAAFI ETPEDGSVPY

 51   LQNLIEKGRY DYDLFKKVVN RNLVRIPQQQ PAPAEITPSY ALGKVLQDAA

101   KIQKQQKDSF IAQDHILFAL FNDSSIQQIF KEAQVDIEAI KQQALELRGN
```

-continued

```
151   TRIDSRGADT NTPLEYLSKY AIDMTEQARQ GKLDPVIGRE EEIRSTIRVL

201   ARRIKSNPCL IGEPGIGKTA IIEGVAQRII DDDVPTILQG AKLFSLDLAA

251   LTAGAKYKGD FEERFKGVLK EIEESKTLIV LFIDEIHMLM GNGKDDAANI

301   LKPALSRGQL KVIGATTNNE YRSIVEKDGA FERRFQKIEV AEPSVRQTVA

351   ILRGLQPKYE IHHGVRILDS ALVTAAQLAK RYLPYRRLPD SALDLVDISC

401   AGVAVARDSK PEELDSKERQ LQLIQVEIKA LERDEDADST TKDRLKLARQ

451   KEASLQEELE PLRQRYNEEK HGHEELTQAK KKLDELENKA LDAERRYDTA

501   TAADLRYFAI PDIKKQIEKL EDQVAEEERR AGANSMIQNV VDSDTISETA

551   ARLTGIPVKK LSESENEKLI HMERDLSSEV VGQMDAIKAV SNAVRLSRSG

601   LANPRQPASF LFLGLSGSGK TELAKKVAGF LFNDEDMMIR VDCSELSEKY

651   AVSKLLGTTA GYVGYDEGGF LTNQLQYKPY SVLLFDEVEK AHPDVLTVML

701   QMLDDGRITS GQGKTIDCSN CIVIMTSNLG AEFINSQQGS KIQESTKNLV

751   MGAVRQHFRP EFLNRISSIV IFNKLSRKAI HKIVDIRLKE IEERFEQNDK

801   HYKLNLTQEA KDFLAKYGYS DDMGARPLNR LIQNEILNKL ALRILKNEIK

851   DKETVNVVLK KGKSRDENVP EEAEECLEVL PNHEATIGAD TLGDDDNEDS

901   MEIDDDLD
```

Provided herein are recombinant Hsp104 protein of wild type amino acid sequence of SEQ ID NO: 1, wherein said sequence comprises a missense mutation in the middle domain thereof. Hsp104WT or Hsp104$^{WT}$ refers to the wild-type sequence. A missense mutation may be in the helix 1 domain of said middle domain, including at position V426. A V426 mutation may be V426L or V426G. As described throughout, the amino acid preceding the number reflects the native (wild-type) amino acid at the numbered position. The amino acid that follows is the amino acid replacement/substitution for the native amino acid. These can also be reflected as, e.g., Hsp104$^{V426L}$ or Hsp104V503L. The symbol A is used to reflect deletions as used herein. Unless otherwise indicated, amino acid positions noted throughout this application reference SEQ ID NO: 1.

A missense mutation may also be placed in the distal loop between the helix 1 and helix 2 domains of said middle domain. This may be a missense mutation is of A437, e.g., A437W. A missense mutation may also be placed in the helix 3 domain of said middle domain. In one embodiment, the missense mutation is within residues 498-507 of SEQ ID NO: 1, inclusive. The missense mutation may be Y507C. Still further, a missense mutation may be placed in the helix 4 domain.

The missense mutation may also be a valine at these residues. For example, the following missense mutations may be included in a recombinant Hsp104 protein according to the invention. D498V, A503C, A503G, A503S, A503V, D504V, Y507A, Y507D, or Y507V.

Still further, the following missense mutations at position 503 may be used: A503C, A503D, A503E, A503F, A503G, A503H, A503I, A503K, A503L, A503M, A503N, A503Q, A503R, A503S, A503T, A503V, A503W, or A503Y. Mutation to proline at this position, i.e., Hsp104$^{A503P}$ was found to enhance toxicity. However, where X is an amino acid other than P, i.e., Hsp104$^{A503X}$, reduced toxicity has been found. Accordingly, any non-proline amino acid may be used to substitute for the alanine at wild-type position 503.

Recombinant proteins described herein may also contain mutations in the substrate-binding pore loops. For example, in combination with a A503 mutation, mutation of the conserved pore loop Y residues (Y257 and Y662) to F (Hsp104$^{DPLF}$, where DPLF refers to substitution of F at the double pore loops) retains suppression of TDP-43 toxicity (for example, Hsp104$^{A503V\text{-}DPLF}$).

A recombinant Hsp104 protein of wild type amino acid sequence of SEQ ID NO: 1 is also provided, wherein said sequence comprises a missense mutation in the NBD1 small domain thereof. The missense mutation can be of N539, including N539D, N539E, N539G, or N539K.

Still further provided are recombinant Hsp104 protein of wild type amino acid sequence of SEQ ID NO: 1 is also provided, wherein said sequence comprises at least one missense mutation in each of two or more domains.

While apparent from the present description including examples, a recombinant Hsp104 protein of wild type amino acid sequence of SEQ ID NO: 1 may be prepared, wherein the sequence comprises a missense mutation yielding a biological activity that reduces aggregation (and toxicity from same) of TDP-43, FUS, or α-synuclein. These include the embodiments described above. In some embodiments, biological activity may reduce toxicity from TDP-43, FUS, and α-syn. In others, TDP-43 and FUS. In others, FUS and α-syn. In others, TDP-43 and α-syn. In still other embodiments, toxicity of one of TDP-43, FUS, and α-syn is reduced.

Recombinant Hsp104 proteins as described herein may be prepared from the wild-type amino acid sequence of SEQ ID NO: 1 or a nucleotide sequence encoding same by conventional methods. For example, a nucleotide sequence may be prepared by site-directed mutagenesis (Agilent-QuikChange™) and confirmed by DNA sequencing. Any of the procedures noted in the Examples may be considered embodiments of the invention as if repeated in this section of the specification.

In one embodiment, yeast are transformed according to standard protocols with a plasmid or linearized plasmid comprising one of the sequences described herein. This 'transgene' may also be expressed in a number of known vector systems, including bacterial and viral systems.

For delivery of a sequence for expression in a subject or in a method for solubilizing misfolded conformations of proteins, including in a mammal and ex vivo, any known expression system may be used. Useful vectors include adenoviral vectors, adeno-associated viral (AAV) vectors (including, without limitation, AAV1, AAV2, AAV3, AAV4, AAV5, AAV6, AAV7, AAV8, AAV9), baculovirus vectors, herpes simplex virus (HSV) vectors, retroviral vectors, lentiviral vectors, vaccinia viral vectors, and RNA virus vectors. In one preferred embodiment, lentiviral vectors are utilized. Vectors useful herein also include pseudotyped vectors. Non-viral gene transfer vectors may also be used, including cationic and other liposomes, DNA-viral conjugates, RNA/DNA oligonucleotides and, surprisingly, naked DNA molecules. Physical procedures, such as hydrodynamics-based and electroporation-based procedures may be used to improve gene transfer efficiency of some non-viral vectors. The particular vector used for expression is not a limitation of the invention. Additional delivery and expression systems are known in the art and are intended to be encompassed herein.

Non-viral delivery may be accomplished by any known means. For example, neuron-targeting ligands used for gene delivery vehicles have included neuropeptides, nerve growth factors, and neuron-specific toxin fragments. By way of non-limited example, tetanus toxin (TeNT), a bacterial protein, is composed of a heavy chain and light chain linked through a disulfide bond. The heavy chain (TeNT Hc) mediates neuron recognition, while the light chain (TeNT Lc) is a metalloprotease that interferes with neurotransmitter activity. Recombinant TeNT Hc has been shown to be internalized by motor neurons and to undergo rapid retrograde transport. Conjugation of TeNT Hc to polycations and complexation with nucleic acid results in neuron-specific gene delivery in vitro. Still others include click-modified cyclodextrins, nanoparticles, cationic lipids, polyethylenimine derivatives, dendrimers, carbon nanotubes, and carbon nanotube-dendrimer combinations.

It is understood that in certain embodiments, the target cell is a neuron. Neurons to which a transgene or expression product is delivered include but are not limited to unipolar, bipolar, and multipolar (including Golgi I or Golgi II) neurons. Also included, without limitation, are basket cells, Betz cells, Lugaro cells, medium spiny neurons, Purkinje cells, pyramidal cells, Renshaw cells, unipolar brush cells, granule cells, anterior horn cells, and spindle cells. The neurons may be cholinergic, GABAnergic, glutamatergic, dopaminergic, or serotonergic.

For use in an AAV (recombinant AAV; rAAV), a minigene is composed of, at a minimum, a heterologous nucleic acid sequence (the transgene, i.e., a modified sequence of wild-type Hsp104 described herein), and its regulatory sequences, and 5' and 3' AAV inverted terminal repeats (ITRs). It is this minigene which is packaged into a capsid protein and delivered to a selected target cell. The transgene is a nucleic acid sequence, heterologous to the vector sequences flanking the transgene, which encodes a polypeptide, protein, or other product, of interest. The nucleic acid coding sequence is operatively linked to regulatory components in a manner which permits transgene transcription, translation, and/or expression in a target cell. The heterologous nucleic acid sequence (transgene) can be derived from any organism. The AAV may comprise one or more transgenes.

Vectors described herein may also include expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters, are known in the art and may be utilized. Useful promoters include, without limitation, the rod opsin promoter, the red-green opsin promoter, the blue opsin promoter, the cGMP-β-phosphodiesterase promoter, the mouse opsin promoter, the rhodopsin promoter, the alpha-subunit of cone transducin, and beta phosphodiesterase (PDE) promoter.

Other useful promoters include transcription factor promoters including, without limitation, promoters for the neural retina leucine zipper (Nrl), photoreceptor-specific nuclear receptor Nr2e3, and basic-leucine zipper (bZIP). Other promoters useful herein include ubiquitous or constitutive promoters, when universal expression of the transgene is desired. In one embodiment, the promoter is selected from the human EF1α promoter, phosphoglycerate kinase-1 (PGK) promoter, and cytomegalovirus (CMV) promoter (optionally with the CMV enhancer). Other examples of constitutive promoters useful herein include, without limitation, the retroviral Rous sarcoma virus (RSV) LTR promoter (optionally with the RSV enhancer), the SV40 promoter, the dihydrofolate reductase promoter, the chicken β-actin (CBA) promoter, and the immediate early CMV enhancer coupled with the CBA promoter.

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. In one embodiment, the inducible promoter is selected from rapamycin/rapalog promoter, the ecdysone promoter, the estrogen-responsive promoter, and the tetracycline-responsive promoter. Examples of other inducible promoters regulated by exogenously supplied compounds which are useful herein, include, the zinc-inducible sheep metallothionine (MT) promoter, the dexamethasone (Dex)-inducible mouse mammary tumor virus (MMTV) promoter, the T7 polymerase promoter system. Other types of inducible promoters which may be useful in this context are those which are regulated by a specific physiological state, e.g., temperature, acute phase, a particular differentiation state of the cell, or in replicating cells only.

Other regulatory sequences useful herein include enhancer sequences. Enhancer sequences useful herein include the IRBP enhancer, immediate early cytomegalovirus enhancer, one derived from an immunoglobulin gene or SV40 enhancer, the cis-acting element identified in the mouse proximal promoter, etc. Selection of these and other common vector and regulatory elements are conventional and many such sequences are available.

Although the description of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as non-human primates, cattle, pigs, horses, sheep, cats, and dogs. Pharmaceutical compositions that are useful in the methods of the invention may be prepared, packaged, or sold in formulations suitable for ophthalmic, oral, parenteral, intranasal, buccal, or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage. The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents.

Controlled- or sustained-release formulations of a pharmaceutical composition of the invention may be made using conventional technology.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, intracranial, intraspinal, intraocular, intravitreal, subcutaneous, intraperitoneal, intramuscular, intrasternal injection, intratumoral, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally acceptable diluent or solvent, such as water or 1,3 butane diol, for example. Other acceptable diluents and solvents include, but are not limited to, Ringer's solution, isotonic sodium chloride solution, and fixed oils such as synthetic mono or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Remington's Pharmaceutical Sciences (1985, Genaro, ed., Mack Publishing Co., Easton, Pa.), which is incorporated herein by reference.

The therapeutic and prophylactic methods of the invention thus encompass the use of pharmaceutical compositions comprising a splice modifying oligonucleotide of the invention to practice the methods of the invention. The precise dosage administered will vary depending upon any number of factors, including but not limited to, the type of animal and type of disease state being treated, the age of the animal and the route of administration.

The compound may be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, etc. The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Methods for suppressing proteotoxicity in a mammal in need thereof, comprising administering a recombinant protein of the invention are provided. By "suppressing", it is meant that proteotoxicity is reduced. In a further embodiment, the term "suppressing" means that proteotoxicity is eliminated. In a further, embodiment, "suppressing" means that proteotoxicity is prevented. Still further provided are methods for suppressing proteotoxicity in a mammal in need thereof, comprising administering a vector comprising a nucleic acid sequence encoding a recombinant protein as described herein.

Also provided is a method for solubilizing a misfolded protein comprising combining said misfolded protein with a recombinant protein described herein or a vector comprising a nucleic acid sequence encoding same. The misfolded protein(s) may be misfolded soluble monomers, misfolded soluble oligomers, disordered aggregates, amyloid fibrils, among others. In embodiments of the application, the misfolded proteins cause or be capable of causing aggregation. In some embodiments, aggregation is with a same protein. In other embodiments, aggregation is with a different protein. In one embodiment, disordered aggregates are of TDP-43, FUS, or α-synuclein.

Also provided are methods of treating a neurodegenerative disease comprising administering a recombinant protein as described herein or a vector comprising a nucleic acid sequence encoding same. The neurodegenerative disease may be amyotrophic lateral sclerosis (ALS) or Parkinson's disease. It may also be Alzheimer's disease or Huntington's disease. It may also be any neurodegenerative disease caused by, or associated with, the misfolding of a protein.

Also provided are methods of identifying a mutated protein of HSP104 of wild type amino acid sequence of SEQ ID NO: 1 that inhibits the aggregation of a mammalian aggregate-prone protein in a yeast cell, comprising: (a) contacting a yeast cell that expresses a chimeric protein comprising a mammalian aggregate-prone protein with said mutated protein under conditions effective to allow the formation of an aggregate in the yeast cell; and (b) determining the ability of said mutated protein to inhibit the aggregation of the aggregate-prone protein in the yeast cell. These methods may also be used in other cells, particularly cells in culture, including in vitro and ex vivo methods. In further embodiments, neuronal cell lines are contemplated, including but not limited to those known in the art for study of one of the above-listed neurodegenerative conditions.

Still further provided are methods for the expression of a target protein in an in vitro or ex vivo translation system, said method comprising preparing a reaction mixture comprising a lysate, a gene coding for the target protein and a gene coding for a recombinant protein as described herein, co-expressing the target protein and recombinant protein, and separating the target protein from the mixture, wherein the co-expression is regulated by metered addition of the gene coding for the recombinant protein or by providing a vector comprising the gene coding for the recombinant protein and a regulatory sequence for regulating induction and strength of the expression.

Also provided are methods for the expression of a target protein comprising co-expression of the target protein with a recombinant protein as described herein. Use of the recombinant proteins described herein and nucleic acid sequences encoding same may also be made in conventional commercial protein expression, production and/or purification systems. By expression of a target protein herein, it is meant that the protein is folded in its native active configuration. In other embodiments, it means that the protein is folded such as to have biological activity. Plasmids comprising a nucleic acid encoding a recombinant protein as described herein are also embodiments of the invention, and such plasmids can be used. Plasmids may be prepared according to standard techniques, or prepared or modified from existing plasmids. For example, plasmids known in the art to be useful in expression protein folding 'chaperones' (proteins that assist the non-covalent folding or unfolding and the assembly or disassembly of other macromolecular structures) are useful. In some embodiments, expression of foldases is advantageous. For example, those described by Hishihara K. et al. (Applied and Environmental Biology) for expression in *E. coli*. (May 1998). However, plasmids for use in other conventional expression systems may also be used. Similarly, the viral and other vectors described above may be used for expression. Included by way of non-limiting example are the chaperone plasmids of TaKaRa Bio Inc., construction methods, and methods of use in expression.

In some embodiments, the target protein is expressed separately from the recombinant protein described herein. This may be by expression of multiple plasmids (or other expression vehicles). The expression vehicles may have separate, similar, or identical sequences regulating their expression.

Further specific embodiments include the following. A method for suppressing proteotoxicity in a mammal in need thereof, comprising administering a vector comprising a nucleic acid sequence encoding a recombinant protein described herein. A method for solubilizing a misfolded protein comprising combining said misfolded protein with a recombinant protein described herein or a vector comprising a nucleic acid sequence encoding same. The misfolded protein may be selected from misfolded soluble monomers, misfolded soluble oligomers, disordered aggregates, and amyloid fibrils. The disordered aggregates may be of TDP-43, FUS, or α-synuclein. A method of treating a neurodegenerative disease comprising administering a recombinant protein as described herein or a vector comprising a nucleic acid sequence encoding same. The neurodegenerative disease may be amyotrophic lateral sclerosis (ALS) or Parkinson's disease. The neurodegenerative disease may be Alzheimer's disease or Huntington's disease. The neurodegenerative disease may be caused by or associated with the misfolding of a protein. A method of identifying a mutated protein of HSP104 of wild type amino acid sequence of SEQ ID NO: 1 that inhibits the aggregation of a mammalian aggregate-prone protein in a yeast cell, comprising: (a) contacting a yeast cell that expresses a chimeric protein comprising a mammalian aggregate-prone protein with said mutated protein under conditions effective to allow the formation of an aggregate in the yeast cell; and (b) determining the ability of said mutated protein to inhibit the aggregation of the aggregate-prone protein in the yeast cell. A method for the expression of a target protein in an in vitro translation system, said method comprising preparing a reaction mixture comprising a lysate, a gene coding for the target protein and a gene coding for a recombinant protein described herein, co-expressing the target protein and recombinant protein described herein, and separating the target protein from the mixture, wherein the co-expression is regulated by metered addition of the gene coding for a recombinant protein described herein or by providing a vector comprising the gene coding for a recombinant protein described herein and a regulatory sequence for regulating induction and strength of the expression. A recombinant Hsp104 protein of wild type amino acid sequence of SEQ ID NO: 1, wherein said sequence comprises a missense mutation yielding a biological activity that reduces aggregation of TDP-43, FUS, or α-synuclein. A method for the expression of a target protein comprising co-expression of said protein with a recombinant protein described herein. A plasmid comprising a nucleic acid encoding a recombinant protein described herein.

The following examples are illustrative only and are not a limitation on the invention described herein. However, the embodiments reflected in these examples are incorporated by reference into the disclosure above.

EXAMPLES

Example 1

Construct Preparation, Disaggregation, and Neuronal Degeneration

A. Experimental Procedures

1. Yeast Strains, Media, and Plasmids

Yeast were WT W303a or the isogenic W303aDhsp104 strain. Dire1 and Datg8 were in BY4741. Standard methods were used for transformation and spot-ting.

All yeast were WT W303a (MATa, can1-100, his3-11,15, leu2-3,112, trp1-1, ura3-1, ade2-1) or the isogenic strain W303aDhsp104 (Sanchez and Lindquist, 1990). Yeast were grown in rich medium (YPD) or in synthetic media lacking the appropriate amino acids. Media was supplemented with 2% glucose, raffinose, or galactose. Vectors encoding TDP-43, FUS, and α-synuclein (pAG303GAL-TDP-43, pAG303GAL-FUS, pAG303GAL-α-synuclein, and pAG304GAL-α-synuclein) were from A. Gitler and M. Duennwald (Johnson et al., 2008, 2009; Sun et al., 2011). pRS416GAL-Hsp104 was from S. Lindquist. All mutations were constructed using QuikChange site-directed mutagenesis (Agilent) and confirmed by DNA sequencing. To assess the importance of the unfolded protein response for suppression of toxicity we used a BY4741Dire1 yeast strain from B. Johnson. To assess the importance of autophagy for suppression of toxicity we used BY4741Datg8 from B. Johnson. Yeast were co-transformed with pAG413GAL-TDP-43, pAG413GAL-FUS, or pAG423GAL-α-synuclein-YFP and pAG416GAL-Hsp104 or vector.

2. Yeast Transformation and Spotting Assays

Yeast were transformed according to standard protocols using polyethylene glycol and lithium acetate (Gietz and Schiestl, 2007). Yeast strains were constructed by first transforming linearized pAG303GAL-TDP-43, pAG303GAL-FUS, or pAG303GAL-α-synuclein-YFP and pAG304GAL-α-synuclein-YFP. Single colonies were selected, grown, and screened for toxicity on galactose inducing medium. Colonies showing a strong toxicity phenotype were selected and subsequently transformed with the pRS416GAL-Hsp104 plasmids. For the spotting assays, yeast were grown to saturation overnight in raffinose supplemented dropout media at 30° C. Cultures were diluted and normalized to A600 nm, grown to an A600 nm=2.0, serially diluted, and spotted in duplicate onto synthetic dropout media containing glucose or galactose. Plates were analyzed after growth for 2-3 days at 30 C.

3. Library Construction and Screening

The pore loop variant library was constructed via QuikChange mutagenesis (Agilent) and DNA shuffling to obtain randomly combined residues at positions Y257 and Y662. The MD variant library was constructed using GeneMorph II EZClone Domain Mutagenesis kit (Agilent) with modifications. Libraries were transformed into yeast harboring pAG303GAL-TDP-43, pAG303GAL-FUS, or pAG303GAL-α-syn. Yeast were grown overnight in raffinose-containing media and plated on galactose-containing media for selection. Select colonies were sequenced by colony PCR. Isolated Hsp104 variants were cloned independently and transformed into yeast to ensure they suppressed toxicity.

To construct a library of pore loop variants, 38 plasmids with all 19 additional amino acids at Y257 and Y662 were constructed using QuikChange mutagenesis. These plasmids were purified by miniprep (QIAGEN) and mixtures composed of equal ratios of the 257X plasmids and 662X plasmids were made. To mix the pore loops and obtain randomly combined residues at each pore loop position, shuffling was performed using an internal SacII restriction enzyme site. The 257X plasmid mixture was digested with BamHI and SacII while the 662X mixture was digested with SacII and XhoI. Digestion products were gel purified using a QIAquick DNA purification kit to eliminate the non-mutagenized pore loop fragment. The pRS416GAL plasmid was digested with BamH1 and XhoI. A mixture containing 0.05 pmol of each product was ligated using T4 DNA ligase according to manufacturer's protocols (NEB). The ligation mixture was transformed in XL10Gold cells, plated, grown, and the DNA was purified by miniprep kit. A representative sampling of single colonies was sequenced to confirm proper ligation and introduction of mutations at each site. The remaining library was scraped off agar plates and purified by miniprep.

The resulting library was transformed into yeast previously transformed with pAG303GAL-TDP-43. Transformation was performed in quadruplicate to ensure that library size was maintained well above the sequence space of the library. The resulting transformants were scraped off selective media and pooled to form the final library. The library was then grown overnight in raffinose-containing media and plated on galactose-containing media for selection. Colonies were selected and sequenced by colony PCR. Suppressors were confirmed by screening on 5-FOA media, which promotes loss of the 416 plasmids. Here, yeast were streaked onto 5-FOA media and single colonies were restreaked in duplicate onto SD-Ura or SD-His plates. Strains that grew on SD-His plates but not SD-Ura plates were selected as hits, and the strains were tested to ensure diminished growth upon galactose induction. The Hsp104 variants were sequenced, cloned independently using QuikChange mutagenesis, and freshly transformed and tested in yeast to ensure they suppressed toxicity.

4. Middle Domain Library Construction

The library of middle domain variants was constructed using a GeneMorph II EZClone Domain Mutagenesis kit (Agilent) with modifications. The middle domain of Hsp104 was amplified by PCR with Mutazyme. The PCR product was purified by gel extraction and subsequently used in a PCR reaction containing pRS416 GAL Hsp104WT and PfuUltraII HS polymerase. The product was then digested with DpnI restriction enzyme and purified using StrataClean resin (Agilent). The product was then ethanol precipitated and transformed by electroporation using ElectroMax DH5a cells in quadruplicate to maintain library size. Mutagenesis was confirmed by sequencing the middle domain of a representative sampling of clones.

5. Hsp104 Variant Toxicity and Thermotolerance

Assessing Toxicity of Hsp104 Variants. W303aDhsp104 yeast were transformed with the indicated 416GAL-Hsp104 plasmid. W303aDhsp104 yeast were transformed with the indicated 416GAL-Hsp104 plasmid. Yeast were diluted and grown in synthetic raffinose medium overnight. Cultures were grown in synthetic raffinose medium to A600 nm=2.0 and spotted onto SD-Ura or SGa1-Ura media and incubated at 30 C or 37 C. Plates were analyzed after 48-72 h of growth.

Thermotolerance Assay W303aDhsp104 yeast were transformed with the indicated 416GAL-Hsp104 plasmid. Yeast were grown to saturation in synthetic raffinose media and then diluted to A600 nm=0.3 in galactose supplemented media. After 4 h growth at 30° C., cells were heat shocked at 50° C. for 0-30 min and then cooled for 2 min on ice. Cultures were serially diluted and spotted on synthetic dropout media supplemented with galactose and the plates were incubated at 30° C. for 2-3 days.

6. Sedimentation Analysis and Immunoblotting

Sedimentation Analysis. Yeast were grown and induced in galactose containing medium for 5 h (TDP-43 and FUS) or 8 h (α-synuclein). Cultures were normalized to A600 nm=0.6 and 100 ml cells were harvested. The cell pellets were resuspended in 10 ml yeast lysis buffer (30 mM HEPES-KOH pH 7.3, 150 mM NaCl, 1% glycerol, 0.5% Triton X-100, 5 mM EDTA, 1 mM DTT, 1 mM PMSF) supplemented with yeast protease inhibitor cocktail (Sigma). Cells were disrupted by 3 passes through a French Press (Emulsiflex C-3) and cleared by centrifugation (6,000×g for 5 min, 4° C.). An aliquot of cleared lysate was reserved as total protein and another aliquot was separated into a soluble and pellet fraction by centrifugation (100,000×g for 15 min, 4° C.). Fractions were then resolved by SDS-PAGE and processed for immunoblot as described below. Known quantities of pure TDP-43 (Origene), FUS (Sun et al., 2011), or GFP were run on each gel to generate calibration curves and ensure quantitation was performed in a linear detection range. Blots were also probed for PGK to confirm separation of the soluble and insoluble fractions. PGK1 is a soluble, cytoplasmic protein and remains in the soluble fraction.

Immunoblotting. Yeast were grown and induced in galactose containing medium for 5 h (TDP-43 and FUS) or 8 h (α-synuclein). Cultures were normalized to A600 nm=0.6, 3 ml cells were harvested, treated in 0.1M NaOH for 5 min at room temperature, and cell pellets were then re-suspended into 1×SDS sample buffer and boiled for 4 min. For heat shock controls, samples were incubated at 42° C. for 20 min prior to processing. Lysates were cleared by centrifugation at 14,000 rpm for 2 min and then separated by SDS-PAGE (4%-20% gradient, Bio-Rad), and transferred to a PVDF membrane. Membranes were blocked in 10% omniblock (American Bioanalytical) in PBS for 1 h at room temperature. Primary antibody incubations were performed at 4° C. overnight. Antibodies used: anti-GFP monoclonal (Roche Applied Science), anti-TDP-43 polyclonal (Proteintech), anti-FUS polyclonal (Bethyl Laboratories), anti-Hsp104 polyclonal (Enzo Life Sciences), anti-PGK monoclonal (Invitrogen), anti-Hsp70 monoclonal (Abcam), and anti-Hsp26 (a kind gift from Johannes Buchner, Technische Universita tMunchen). For quantitative immunoblotting, standard protein calibration curves were included on each gel, and blots were processed using LI-COR Odyssey Fc Imaging system.

7. Fluorescence Microscopy, Imaging, and Statistical Analysis

TDP-43 was imaged by appending a GFPS11 tag to its C terminus and separately expressing the GFPS1-10 fragment to promote GFP reassembly (Cabantous and Waldo, 2006). These fragments were then subcloned into pAG303GAL-ccdB (TDP-43-GFPS11) or pAG415GAL-ccdB (GFPS1-10). Strains were constructed by integrating pAG303GAL-TDP-43-GFPS11 and pAG305GAL GFPS1-10 or pAG303GAL-FUS-GFP using the same strategy as described above. Single colonies were selected and screened by toxicity, and colonies displaying high levels of toxicity were selected and grown. Yeast were grown for microscopy as for immunoblotting. After 5 h induction at 30° C. (8 h for α-synuclein strains), cultures were harvested and processed for microscopy. For TDP-43, cells were harvested and fixed in 70% ethanol for 10 min at room temperature. Cells were then washed in water 3 times, and then stained with 4',6-diamidino-2-phenylindole in Vectashield mounting medium (Vector Laboratories) to visualize nuclei. For FUS, all imaging was performed using live cells, as fixing was noted to diminish foci. Quantification of foci was performed using live, untreated cells. To visualize nuclei for the images presented in this paper, live cells were treated with Hoechst dye. Images were collected at 100× magnification using a Leica-DMIRBE microscope and processed using ImageJ software.

Fluorescent microscopy was performed using a Nikon Eclipse E800 epifluorescence microscope equipped with an Endow GFP HYQ filter cube (Chroma Technology). A Cool Snap CCD camera (Photometrics) driven by MetaMorph software (Molecular Devices) was used to acquire images. DNA gel images were acquired using the Fujifilm Image Reader LAS-4000. One-way ANOVA was used to analyze the averages from each construct as well as α-synuclein alone. The post-hoc Dunnett's multiple comparisons test was used to compare α-synuclein alone to each generated construct. A P value<0.05 was deemed statistically significant. Statistical analysis was performed using Graph Pad Prism Software.

8. Analysis for Dopaminergic Neuron Death in *C. elegans*

Generation of Transgenic Nematodes. *C. elegans* were injected and maintained through previously published methods (Berkowitz et al., 2008a, 2008b). Briefly, 30-40 young adult worms (UA44 [baIn11{$P_{dat-1}$::gfp, $P_{dat-1}$::α-synuclein}]) were injected with a solution of 50 ng/ml plasmid with each of the 4 Hsp104 constructs cloned into pDEST-dat-1 plasmid via Gateway technology (Invitrogen). This solution also contains 1-3 ng/ml of a plasmid [Pmyo-2::mCherry (pharyngeal expression)], which serves as a phenotypic marker for transformation. Injected hermaphrodites (P0) were placed 8-10 per medium NGM plate to recover for 2 days. After 2 days, each plate was screened for progeny (F1) expressing the coinjection marker and isolated to individual small NGM plates. After 2 days, F1-containing plates were screened for stable expression of the visible marker. For each construct at least three distinct stable lines were isolated. In all, three separate transgenic lines for each hsp104 construct were generated and analyzed. The different lines generated through this method are designated as: UA256(baEx147[$P_{dat-1}$::Hsp104 WT, $P_{myo-2}$::mCherry]; baIn11[$P_{dat-1}$::α-syn, $P_{dat-1}$::GFP]), UA257(baEx148 [$P_{dat-1}$::Hsp104 null, $P_{myo-2}$::mCherry]; baIn11[$P_{dat-1}$::α-syn, $P_{dat-1}$::GFP]), UA259(baEx150[$P_{dat-1}$::Hsp104$^{A503S}$, $P_{myo-2}$::mCherry]; baIn11[$P_{dat-1}$::α-syn, $P_{dat-1}$::GFP]), UA262(baEx153[$P_{dat-1}$::Hsp104$^{A503-DPLF}$, Pmyo-2::mCherry]; baIn11[$P_{dat-1}$::α-syn, $P_{dat-1}$::GFP]).

Analysis for Dopaminergic Neuron Death

Age synchronized worms were generated by allowing 50 transgenic adults on a medium NGM plate to lay eggs for three hours. After which, the adults were completely removed (day 0). At day 7 and day 10 of analysis, 40 randomly selected worms with the marker transgene were placed in 3 mM Levamisol for paralysis and transferred to a 2% agarose pad on a glass microscope slide. Worms have 8 dopaminergic neurons visible through Pdat-1::gfp, which fade in an age dependent manner due to the accumulation of α-synuclein. Only the six neurons in the anterior portion of the worm were analyzed. Each worm is given a score of "Wild type" when there is a full complement of visible, anterior dendritic processes. However, a worm that is missing one or more dendritic processes has the number of neurons degenerating scored and is considered "Not Wild Type." 30 worms from each slide were analyzed in this manner and recorded. This process was repeated three to four times for each construct, which marks the results of one stable line. In total three separate stable lines were analyzed in this manner.

9. RNA Isolation and RT-PCR

RNA isolation and RT-PCR was performed on worms using previously published methods (Harrington et al., 2012). Briefly, 50 young adult hermaphrodites expressing the coinjection marker mCherry in the pharynx were cleaned of bacteria in M9 and transferred into a 10 ml solution of 10% Single Worm Lysis Buffer (10 mM Tris, pH 8.3, 50 mM KCl, 2.5 mM MgCl2, 0.45% NP-40, 0.45% Tween 20, 0.01% gelatin, 60 mg of proteinase K) and frozen at −80° C. for up to 6 hr. After thawing, 100 ml of TRI reagent (Molecular Research Center) was added to each sample and incubated at room temperature (RTP) for 10 min. Samples were freeze-thawed in liquid N2, vortexed for 15 s with 10 ml of 1-bromo-3-chloropropane (AcrosOrganics), incubated for 10 min at RTP, and centrifuged for 20 min at 13,200 rpm at 4° C. Approximately 50 ml of supernatant was transferred to an RNase free tube and mixed with 1.5 ml glycoblue (Ambion) and 50 ml of chilled, −20° C. isopropanol and stored overnight (12 hr) at −20° C. After incubation, samples were centrifuged for 20 min at 13,200 rpm at 4° C. and supernatant was discarded. The pellet was washed with 100 ml of RNase-free ethanol (75%) and resuspended in 10 ml MB grade DEPC-treated water, 1 ml RQ1 RNase-free DNase (Promega), and 1 ml RQ1 DNase buffer, which was then incubated at 37° C. for 15 min. After incubation, 1 ml RQ1 DNase stop buffer was added to each sample and incubated at 65° C. for 10 min. RT-PCR was performed using SuperScript III RT (Invitrogen) using Oligo dT(20) to prime 1 mg of mRNA following the manufacturers protocol. cDNA amplification was performed using Phusion polymerase (Finnzymes) with the following primers:

cdk-5

(SEQ ID NO: 2)
5' CGTTGCGTTGAAAAGAGTAAGG, cdk-5

(SEQ ID NO: 3)
3' CCGGCATTTGAGGATCTCTGC,

α-synuclein (SEQ ID NO: 4)
5' GGATGTATTCATGAAAGGACTTTCAAAG,

α-synuclein (SEQ ID NO: 5)
3' GGCTTCAGGTTCGTAGTCTTG, hsp104

(SEQ ID NO: 6)
5' CACTGCTGCTCAATTAGCCAAGCG, hsp104

(SEQ ID NO: 7)
3' CACGACTTCAGATCACGTTCCATATG.

Amplified products were separated on a 0.8% agarose gel and visualized using GelRed staining (Biotium).

10. Protein Purification

Proteins were purified as recombinant proteins in *E. coli* using standard techniques Hsp104 or HAP proteins were expressed and purified as untagged proteins from *E. coli*. Proteins were overexpressed in BL21(DE3) RIL. Cells were harvested, lysed with lysis buffer (50 mM Tris pH 8.0, 10 mM MgCl2, 2.5% glycerol, 2 mM b-mercaptoethanol) supplemented with protease inhibitors, and the protein was purified using Affi-Gel Blue Gel (Bio-Rad). The protein was eluted with elution buffer (50 mM Tris pH 8.0, 1M KCl, 10 mM MgCl2, 2.5% glycerol, 2 mM b-mercaptoethanol). The eluate was buffer exchanged into high salt storage buffer (40 mM HEPES-KOH pH 7.4, 500 mM KCl, 20 mM MgCl2, 10% glycerol, 1 mM DTT). The protein was then further purified by ResourceQ anion exchange chromatography using running buffer Q (20 mM Tris pH 8.0, 0.5 mM EDTA, 5 mM MgCl2, 50 mM NaCl) and eluted with a linear gradient of buffer Q+ (20 mM Tris pH 8.0, 0.5 mM EDTA, 5 mM MgCl2, 1M NaCl). Immediately before loading the column, the protein was diluted to a final concentration of 10% in buffer Q supplemented to 150 mM NaCl and loaded onto the column using a 50 ml Superloop. The eluted protein was then concentrated and exchanged into high salt storage buffer and used immediately. Hsp104 concentrations refer to the hexamer concentration. C-terminally His-tagged ClpP was overexpressed in BL21(DE3) *E. coli* cells and purified using Ni Sepharose 6 Fast Flow following standard procedures. The eluted protein was concentrated and exchanged into ClpP Buffer (20 mM Tris pH 7.5, 100 mM KCl, 0.1 mM EDTA, 10% glycerol, 5 mM DTT). GroELtrap was purified as described (Doyle et al., 2007). α-synuclein was purified as described (Lo Bianco et al., 2008). GST-TEV-TDP-43 and GST-TEV-FUS were purified as described (Johnson et al., 2009; Sun et al., 2011). RepA1-70-GFP was purified by expressing N-terminally His-tagged protein in *E. coli* and purifying from inclusion bodies in 6M urea. Urea was removed by dialysis and the protein was applied to Ni-NTA beads. The eluted protein was then used with the tag. Firefly luciferase and FITC-casein were from Sigma and creatine kinase was from Roche. Hsc70 and Hdj2 were from Enzo Life Sciences. Ssa1, Ydj1, and Sse1 were purified as described (Raviol et al., 2006; Shorter and Lindquist, 2008).

11. ATPase Activity

Hsp104 (0.042 μM hexamer) was incubated with ATP (1 mM) for 5 min at 25° C. ATPase activity was assessed by inorganic phosphate release using a malachite green detection kit (Innova). Background hydrolysis was determined at time zero and subtracted.

12. Luciferase Reactivation

Luciferase reactivation was performed as described (DeSantis et al., 2012; Glover and Lindquist, 1998). Briefly, to assemble aggregates, firefly luciferase (50 μM) in luciferase-refolding buffer (LRB: 25 mM HEPES-KOH pH 7.4, 150 mM KAOc, 10 mM MgAOc, 10 mM DTT) plus 8M urea was incubated at 30° C. for 30 min. The sample was then rapidly diluted 100-fold into LRB. Aliquots were snap frozen and stored at −80° C. until use. Aggregated luciferase (50 nM) was incubated with Hsp104 (0.167 μM hexamer) with ATP (5.1 mM) and an ATP regeneration system (1 mM creatine phosphate, 0.25 mM creatine kinase) in the presence or absence of Hsc70 (0.167 mM) and Hdj2 (0.167 μM) for 90 min at 25° C. In some reactions (FIG. 6C), Hsc70 concentration was 0.167 μM and Hdj2 concentration was 0.073 mM. In other reactions (FIG. 6C), Hsc70 and Hdj2 were replaced with Ssa1 (0.167 μM) and Ydj1 (0.073 μM) or Ssa1 (0.167 μM), Ydj1 (0.073 μM), and Sse1 (0.043 μM). At the end of the reaction, luciferase activity was assessed with a luciferase assay system (Promega). Recovered luminescence was monitored using a Tecan Infinite M1000 plate reader.

For the mutant doping experiments, the Hsp104A503V variants (Hsp104A503V-DWA: (K218T:A503V:K620T), Hsp104A503V-DPLA:(Y257A:A503V:Y662A), Hsp104A503V-DWB: (E285Q:A503V:E687Q), Hsp104A503V-DPLA-DWB: (Y257A:E285Q:A503V:Y662A:E687Q)) were mixed with Hsp104A503V in varying ratios to give a total concentration of 0.5 μM Hsp104 hexamer, and the experiments were performed as described. Hsc70 and Hdj2 were omitted for these experiments.

We employed the approach of Reinstein and colleagues to simulate the distribution of Hsp104A503V and Hsp104A503V mutant sub-units within a given population of Hsp104 hexamers (Werbeck et al., 2008). Thus, we employed the binomial distribution:

$$P(x) = \binom{n}{x} p^x (1-p)^{n-x},$$

where P is the probability that a hexamer (therefore, n=6) contains x mutant subunits and p is the probability that a mutant subunit is incorporated. Experiments demonstrated that A503V mutant and A503V subunits have a similar probability of being incorporated into a hexamer. Consequently, p is calculated as the molar ratio of A503V mutant and A503V protein present:

$$p = \frac{Hsp104_{A503V\text{-}mut}}{(Hsp104_{A503V\text{-}mut} + Hsp104_{A503V})}.$$

Therefore, for any specified percentage of mutant subunits the probability distribution of Hsp104 hexamers containing 0, 1, 2, 3, 4, 5 or 6 mutant subunits can be derived. Activity versus p plots could then be generated assuming each A503V subunit makes an equal contribution to the total activity (one-sixth per subunit). Consequently, if subunits within the hexamer operate independently then activity should decline in a linear manner upon incorporation of defective mutant subunits. Conversely, if subunits are coupled then a specific number of subunits will be sufficient to eliminate activity. Thus, zero activity is assigned to hexamers that are in breach of a specific threshold number of mutant subunits. In this way, we can generate activity versus p plots if we assume that 1 or more, 2 or more, 3 or more, 4 or more, or 5 or more mutant subunits are required to eliminate activity.

To model the stimulatory effect of $Hsp104^{A503V\text{-}DWB}$ subunits on $Hsp104^{A503V}$ activity we employed the binomial distribution as above, but imposed an additional rule whereby a mutant subunit stimulates the activity of an adjacent A503V subunit by a factor of s, but exerts an inhibitory effect if it is adjacent to a mutant subunit (Moreau et al., 2007). To model this behavior, we scored each subunit-subunit interface of every possible hetero-hexamer in each possible configuration as follows: interfaces were scored as 1/6 if at an A503V-A503V junction, s/6, if at an A503V-A503V-DWB junction, or 0 if at an A503V-DWB-A503V-DWB junction. Activity was then normalized to the predicted hetero-hexamer population as defined by the binomial distribution above. FIG. 6J shows the effect of increasing amounts of stimulation denoted by the variable s.

13. RepA1-70-GFP Unfolding

RepA1-70-GFP unfolding was as described previously (Doyle et al., 2007).

14. FITC-Casein Degradation and Binding

FITC-Casein Degradation Assays. FITC-casein (0.1-50 μM) was incubated with HAP or HAPA503V (1 μM hexamer) and ClpP (21 μM monomer) at 25° C. ATP (5 mM) and an ATP-regenerating system were included in all reactions. Degradation of FITC-casein was monitored by measuring fluorescence (excitation 490 nm, emission 520 nm) using a Tecan Safire2 microplate reader. To calculate initial rate, a linear fit of the first 2.5 min of the reaction was constructed and the slope was calculated. The initial rates were plotted against FITC-casein concentration to determine Km using Graph Pad Prism Software.

FITC-Casein Binding Assays. 6 nM FITC-casein was incubated with increasing concentrations (0-5 μM) of Hsp104WT or Hsp104A503V with 2 mM ATPgS in LRB for 10 min at 25° C. Fluorescence polarization was measured (excitation 470 nm, emission 520 nm) on a Tecan Infinite M1000 plate reader.

15. FRET and Subunit Mixing Assays

We labeled Hsp104A503V with Alexa-Fluor 488 (AF488) as the donor and Hsp104A503V-DWB with Alexa-Fluor 546 (AF546) as the acceptor as described with minor modifications (DeSantis et al., 2012). The Hsp104 variants were labeled in high-salt storage buffer (40 mM HEPES-KOH pH 7.4, 500 mM KCl, 20 mM $MgCl_2$, 10% glycerol) and incubated with TCEP (3-10 mM) for 15 min on ice to ensure cysteine residues were reduced. The protein was then labeled with a 20-fold molar excess of dye over Hsp104. Approximately 1.5-2 molecules of dye were incorporated per monomer. To test subunit mixing, we used identical conditions to the luciferase assays. Hsp104A503V and Hsp104A503V-DWB were mixed in a 1:1 ratio and mixtures comprised of 0.5 μM hexamer supplemented with 5 mM ATP and ATP regenerating system were tested for FRET. As a negative control, reactions were prepared in 1M NaCl to inhibit hexamerization. Reactions were also prepared with 1 μM Hsp104 hexamer, which increases hexamerization and thereby FRET. Equilibrated samples were excited at the donor excitation wavelength of 475 nm. To monitor FRET, fluorescence emission spectra were collected from 500-650 nm. FRET efficiency was calculated from AF488-Hsp104A503V emission (522 nm) as 1-(FDA/FD), where FDA is the measured AF488-Hsp104A503V fluorescence in the presence of AF546-Hsp104A503V-DWB (acceptor) and FD is the AF488-Hsp104A503V fluorescence in the presence of unlabeled Hsp104A503V-DWB. These FRET efficiencies are very similar to those reported for Hsp104WT (DeSantis et al., 2012).

16. α-syn Fibril Disaggregation

α-syn (80 mM) was assembled into fibrils via incubation in 40 mM HEPES-KOH (pH 7.4), 150 mM KCl, 20 mM MgCl2, 1 mM dithiothreitol for 48 hr at 37° C. with agitation. α-syn fibrils (0.5 μM monomer) were incubated without or with Hsp104WT, Hsp104A503V, Hsp104A503S, or Hsp104A503V-DPLF (0.5 or 5 μM) plus ATP (10 mM) and ARS (20 mM creatine phosphate and 0.5 mM creatine kinase) for 1 hr at 30° C. Disaggregation was assessed by Thioflavin-T (ThT) fluorescence, sedimentation analysis, and EM (Lo Bianco et al., 2008).

α-synuclein was assembled into fibrils as described (Lo Bianco et al., 2008). Briefly, α-synuclein (80 mM) was incubated in KHMD (40 mM HEPES-KOH, pH 7.4, 150 mM KCl, 20 mM MgCl2, 1 mM DTT) for 48 h at 37° C. with agitation (1,400 rpm in an Eppendorf ther-momixer). α-synuclein fibrils (0.5 μM monomer) were incubated in the presence or absence of Hsp104WT, Hsp104A503V, Hsp104A503S, or Hsp104A503V-DPLF (0.5 or 5 mM) plus ATP (10 mM) and regeneration system (20 mM creatine phosphate and 0.5 mM creatine kinase) for 1 h at 30° C. Fibril disassembly was assessed using Thioflavin-T, sedimentation analysis, or electron microscopy as described (Lo Bianco et al., 2008).

17. TDP-43 and FUS Disaggregation

To generate TDP-43 and FUS aggregates, GST-TEV-TDP-43 (6 mM) or GST-TEV-FUS (6 mM) was incubated with TEV protease in 50 mM Tris-HCl (pH 7.4), 50 mM KCl, 5 mM MgCl2, 0.2 M trehalose, and 20 mM glutathione. FUS was aggregated for 90 min at 25 C without agitation, by which time all the FUS had aggregated (Sun et al., 2011). TDP-43 was aggregated for 4 hr at 25° C. with agitation, by which time all the TDP-43 had aggregated (Johnson et al., 2009). TDP-43 or FUS aggregates (3 μM monomer) were incubated for lhr at 30° C. with Hsp104WT, Hsp104A503V, or Hsp104A503S (1 μM) plus or minus Ssa1 (1 μM), Ydj1 (0.44 μM), and Sse1 (0.26 μM) plus ATP (10 mM) and ARS (20 mM creatine phosphate and 0.5 μM creatine kinase). Disaggregation was assessed via turbidity (absorbance at 395 nm) and EM (Johnson et al., 2009; Sun et al., 2011).

To generate TDP-43 and FUS aggregates, GST-TEV-TDP-43 (6 μM) or GST-TEV-FUS (6 μM) were incubated with TEV protease (Invitrogen) in assembly buffer (50 mM TrisHCl pH 7.4, 50 mM KCl, 5 mM MgCl2, 0.2M trehalose, and 20 mM glutathione). FUS was aggregated for 90 min at 25° C. without agitation, by which time all the FUS had converted to the aggregated state (Sun et al., 2011). TDP-43 was aggregated for 4 h at 25° C. with agitation (1,400 rpm in an Eppendorf thermomixer), by which time all the TDP-43 had converted to the aggregated state (Johnson et al., 2009). TDP-43 or FUS aggregates (3 mM monomer) were then incubated for 60 min at 30° C. with the indicated combination of Hsp104WT, Hsp104A503V, or Hsp104A503S (1 mM) with or without Ssa1 (1 mM), Ydj1 (0.44 mM), and Sse1 (0.26 mM) plus ATP (10 mM) and regeneration system (20 mM creatine phosphate and 0.5 mM creatine kinase). Disaggregation was assessed via turbidity (absorbance at 395 nm) and electron microscopy as described (Johnson et al., 2009; Sun et al., 2011).

B. Results

1. Substrate-Binding Tyrosines in Hsp104 Pore Loops Are Optimal for Disaggregation.

Hsp104 is adapted for disaggregation of the yeast proteome. We sought to engineer Hsp104 variants to disaggregate TDP-43, an RNA-binding protein with a prion-like domain (Cushman et al., 2010), which has no yeast homolog and is not a natural Hsp104 substrate. A yeast model of TDP-43 proteinopathies has been developed in which TDP-43 is overexpressed via a galactose-inducible promoter (Johnson et al., 2008). TDP-43 aggregates in the cytoplasm and is toxic to yeast, which phenocopies TDP-43 pathology in disease and has enabled identification of common ALS genetic risk factors (Elden et al., 2010). To explore Hsp104 sequence space against TDP-43 toxicity, we employed Dhsp104 yeast to assess Hsp104 variants in the absence of wild-type (WT) Hsp104. TDP-43 is highly toxic in Dhsp104 yeast and Hsp104WT provides minimal rescue of toxicity (Johnson et al., 2008). Thus, Dhsp104 yeast provide a platform to isolate more active Hsp104 variants. Each Hsp104 monomer contains two nucleotide-binding domains (NBD1 and NBD2) as well as an N-terminal, middle, and C-terminal domain (DeSantis and Shorter, 2012). Hsp104 forms ring-shaped hexamers with a central pore through which substrate is threaded. To alter substrate specificity, we assessed Hsp104 variants bearing mutations in Hsp104's two substrate-binding pore loops (DeSantis and Shorter, 2012). We mutated the conserved pore loop residues, Y257 and Y662, which mediate substrate binding and translocation (Tessarz et al., 2008) to all amino acids and screened this library of 400 variants for rescue of TDP-43 toxicity. After several rounds of selection, nearly all the variants possessed Y at one or more often both pore-loop positions. None of the pore-loop Hsp104 variants were more active than Hsp104WT in rescuing TDP-43 toxicity. Thus, Y257 and Y662 are likely optimal for disaggregation.

2. Select Missense Mutations in the Middle Domain Potentiate Hsp104 Activity.

Figure 1A:
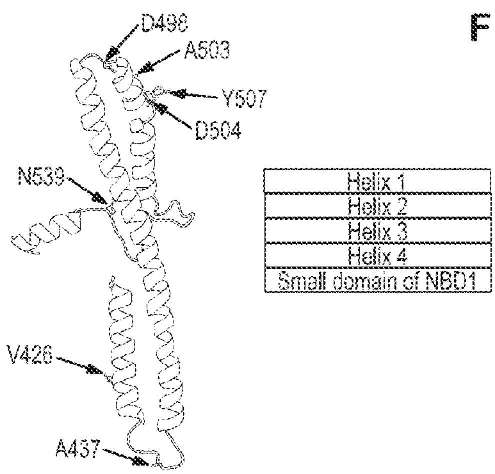
FIG. 1A-D provides Hsp104 MD Variants Rescue Diverse Proteotoxicity Models.

Next, we explored the coiled-coil middle domain (MD) of Hsp104, which is less conserved than the substrate-binding pore loops. MD variants can have unexpected gain-of-function phenotypes (Schirmer et al., 2004). The Hsp104 MD (residues 411-538; FIG. 1A) facilitates optimal ATPase activity, communication between NBD1 and NBD2, intrinsic disaggregase activity, and interactions with Hsp70 during disordered aggregate dissolution (DeSantis and Shorter, 2012). We randomly mutagenized the MD and screened this Hsp104 library against α-syn, FUS, or TDP-43 toxicity (Johnson et al., 2008; Outeiro and Lindquist, 2003; Sun et al., 2011). We employed Dhsp104 yeast, as deletion of Hsp104 does not affect α-syn, FUS, or TDP-43 toxicity (Johnson et al., 2008; Ju et al., 2011). We identified several Hsp104 variants that potently rescued α-syn, FUS, and TDP-43 toxicity, whereas Hsp104WT was ineffective (FIG. 1B). Potentiated Hsp104 variants had a missense mutation in helix 1 (Hsp104V426L) or in the distal loop between helix 1 and 2 (Hsp104A437W) or in helix 3 (Hsp104A503V or Hsp104Y507C)(FIGS. 1A and 1B). Unexpectedly, we uncovered an enhanced variant with a missense mutation in the NBD1 small domain (Hsp104N539K)(FIGS. 1A and 1B). Thus, the MD or small domain of NBD1 can be mutated to potentiate Hsp104 activity against α-syn, FUS, and TDP-43.

Two potentiating mutations, A503V and Y507C, lie in MD helix3. Thus, we performed a valine scan of helix 3

Figure 1D:
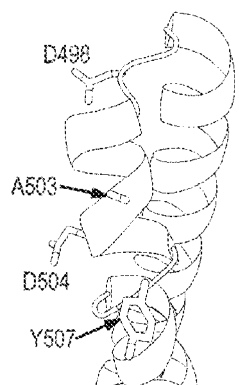
Figure 1B:
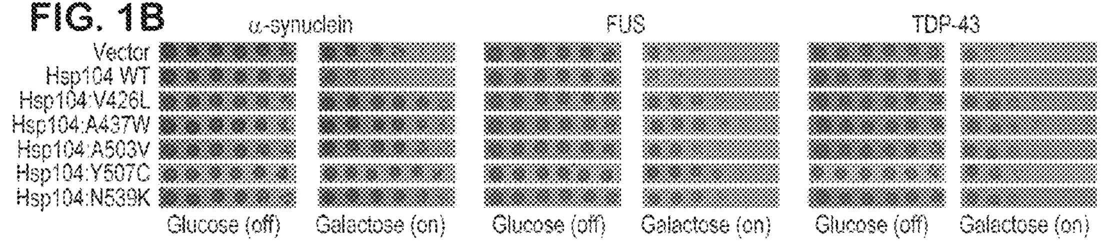
Figure 1C:
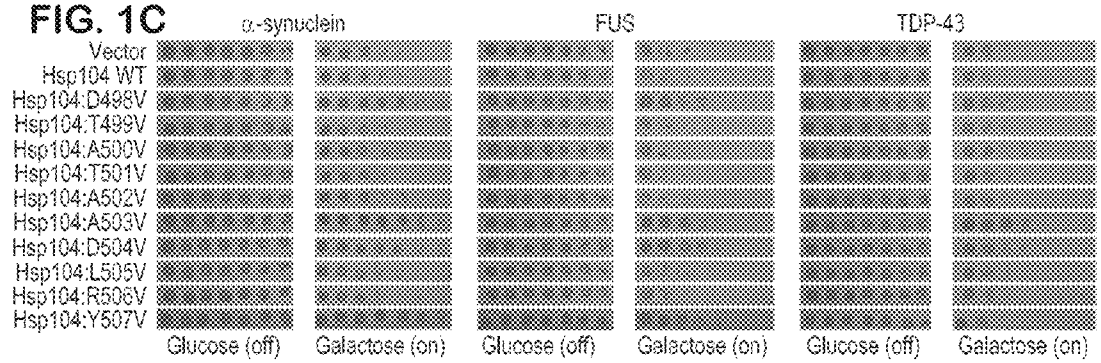

(residues 498-507) in search of additional enhanced variants (FIGS. 1C and 1D). Most helix-3 valine substitutions behaved like Hsp104WT (FIG. 1C). However, Hsp104D504V suppressed α-syn, FUS, and TDP-43 toxicity (FIG. 1C). Hsp104D498V and Hsp104Y507V suppressed FUS and α-syn toxicity, but not TDP-43 toxicity (FIG. 1C). Thus, select missense mutations in helix 3 engender potentiated Hsp104 variants with altered substrate specificity.

Two different Y507 mutations yielded enhanced variants. Thus, we explored other substitutions at this position. Hsp104Y507A, Hsp104Y507C, and Hsp104Y507D rescued α-syn, FUS, and TDP-43 toxicity (FIG. 8A). Likewise, additional substitutions at D504 (to C), V426 (to G), or N539 (to E, D, G, or K) yielded potentiated Hsp104 variants against FUS toxicity (FIGS. 8A and 8B). Thus, diverse mutations at specific positions in the MD enhance Hsp104 activity.

3. Hsp104A503X Variants Suppress TDP-43 Toxicity and Promote Its Proper Localization.

Hsp104A503V was among the strongest suppressors of α-syn, FUS, and TDP-43 toxicity, and so we explored this position further and mutated A503 to all amino acids. None of these Hsp104 variants were toxic to yeast when overexpressed at 30° C. (FIG. 9). Mutation of A503 to V, S, or C suppressed TDP-43 toxicity; Hsp104A503C most strongly suppressed TDP-43 toxicity, followed by Hsp104A503S and Hsp104A503V (FIGS. 2A, 2B, and 10A). Surprisingly, mutation of A503 to nearly any residue suppressed TDP-43 toxicity, whereas Hsp104A503P enhanced toxicity (FIGS. 2A and 10A). Indeed, we could now mutate the conserved pore loop Y residues (Y257 and Y662) to F (Hsp104A503V-DPLF) and retain suppression of TDP-43 toxicity (FIG. 2A). Rescue of TDP-43 toxicity was not due to lower levels of TDP-43, which were roughly equal across strains (FIG. 2C). Likewise, rescue could not be explained by higher Hsp104 expression. Hsp104 variants were expressed at slightly lower levels than Hsp104WT (FIG. 2C). Quantitative immunoblot revealed that Hsp104 hexamer:TDP-43 ratios were ~1:1.31 for Hsp104WT and ~1:2.20 for Hsp104A503V. Hsp70 and Hsp26 levels were also similar for all strains, indicating that Hsp104 variants do not induce a heat shock response (HSR; FIG. 2C). Hsp104A503V expression from the native Hsp104 promoter (which is weaker than the galactose promoter) suppressed TDP-43 toxicity (FIGS. 11A and 11B). Here, quantitative immunoblot revealed that Hsp104 hexamer:TDP-43 ratios were ~1:1.70 for Hsp104WT and ~1:4.55 for Hsp104A503V. Thus, even low Hsp104A503V levels rescued TDP-43 toxicity. Finally, Hsp104A503V, Hsp104A503S, and Hsp104A503V-DPLF rescued TDP-43 toxicity in Dire1 (to disrupt the unfolded protein response [UPR]) and Datg8 (to disrupt autophagy) strains (FIG. 2D). Thus, neither the UPR nor autophagy is needed for enhanced Hsp104 variants to rescue TDP-43 toxicity.

TDP-43 normally shuttles between the nucleus and cytoplasm. However, in ALS, TDP-43 is usually depleted from the nucleus and aggregated in the cytoplasm of degenerating motor neurons (Robberecht and Philips, 2013). Indeed, cytoplasmic TDP-43 aggregates persist upon Hsp104WT overexpression (FIG. 2E). By contrast, Hsp104A503V eliminated cytoplasmic TDP-43 aggregates and ~46% of cells had nuclear TDP-43 localization (FIG. 2E). Accordingly, Hsp104A503V reduced the amount of insoluble TDP-43 by ~57%, whereas Hsp104WT was ineffective (FIG. 2F). Thus, Hsp104A503V eliminates TDP-43 aggregation and toxicity and restores TDP-43 to the nucleus. These phenotypes are a therapeutic goal for ALS and other TDP-43 proteinopathies. Several suppressors of TDP-43 toxicity have been isolated in yeast, but none clear cytoplasmic TDP-43 aggregates (Sun et al., 2011). Thus, our enhanced Hsp104 variants are the first (to our knowledge) genetic suppressors that eradicate TDP-43 aggregates and restore TDP-43 to the nucleus.

4. Hsp104A503X Variants Suppress FUS Toxicity and Aggregation.

Next, we tested Hsp104A503X variants for rescue of FUS toxicity in yeast. FUS, like TDP-43, is a nuclear RNA-binding protein with a prion-like domain that forms cytoplasmic aggregates in degenerating neurons of FUS proteinopathy patients and in yeast (Ju et al., 2011; Robberecht and Philips, 2013; Sun et al., 2011). As for TDP-43, mutation of A503 to any amino acid except P strongly suppressed FUS toxicity, as did Hsp104A503V-DPLF (FIGS. 3A, 3B, and 10B). Hsp104A503G most strongly suppressed FUS toxicity (FIGS. 3A, 3B, and 10B). Rescue of FUS toxicity by Hsp104A503X variants (or Hsp104D498V or Hsp104D504V) could not be explained by lower FUS levels, induction of Hsp70 or Hsp26 in a HSR, or higher Hsp104 levels (FIG. 3C). Indeed, quantitative immunoblot revealed that Hsp104 hexamer:FUS ratios were ~1:5.13 for Hsp104WT and ~1:3.25 for Hsp104A503V. Even low Hsp104A503V levels expressed from the natural Hsp104 promoter suppressed FUS toxicity (FIGS. 11C and 11D). Here, quantitative immunoblot revealed that Hsp104 hexamer:FUS ratios were ~1:5.21 for Hsp104WT and ~1:9.58 for Hsp104A503V. Rescue of FUS toxicity by Hsp104A503V, Hsp104A503S, and Hsp104A503V-DPLF occurred in Dire1 strains and Datg8 strains (FIG. 3D). Thus, the UPR and autophagy are not required for potentiated Hsp104 variants to suppress FUS toxicity.

Hsp104A503V eliminated FUS aggregates, whereas Hsp104WT had no effect (FIG. 3E). In contrast to TDP-43, FUS was now diffuse in the cytoplasm (FIG. 3E) because the yeast nuclear transport machinery fails to decode the FUS PY-NLS (Ju et al., 2011). Hsp104A503V reduced the amount of insoluble FUS by ~49%, whereas Hsp104WT was ineffective (FIG. 3F). Genome-wide overexpression screens have yielded several suppressors of FUS toxicity in yeast, but none that solubilize FUS inclusions (Ju et al., 2011; Sun et al., 2011). Thus, potentiated Hsp104 variants are the first (to our knowledge) genetic suppressors that eradicate FUS aggregates.

5. Hsp104A503X Variants Suppress α-syn Toxicity and Promote Its Proper Localization.

Next, we tested Hsp104A503X variants against α-syn toxicity in yeast. α-syn is a lipid-binding protein that localizes to the plasma membrane but forms cytoplasmic inclusions in degenerating dopaminergic neurons in PD and in yeast (Cushman et al., 2010; Outeiro and Lindquist, 2003). Nearly all Hsp104A503X variants sup-pressed α-syn toxicity except Hsp104A503P, which had no effect (FIGS. 4A, 4B, and 10C). By contrast, Hsp104WT slightly enhanced α-syn toxicity (FIGS. 4A and 4B). Hsp104A503V-DPLF suppressed α-syn toxicity, though not as strongly as Hsp104A503V (FIG. 4A). Rescue of α-syn toxicity by Hsp104A503X variants (or Hsp104D504V) could not be explained by lower α-syn levels, induction of Hsp70 or Hsp26 in a HSR, or higher Hsp104 levels (FIG. 4C). Quantitative immunoblot indicated that the Hsp104 hexamer:α-syn ratios were ~1:2.43 for Hsp104WT and ~1:2.84 for Hsp104A503V. Expression of Hsp104A503V from the Hsp104 promoter suppressed α-syn toxicity, whereas Hsp104WT had no effect (FIGS. 11E and 11F). Here, quantitative immunoblot indicated that the Hsp104 hexamer:α-syn ratios were ~1:3.03 for Hsp104WT and ~1:5.79 for Hsp104A503V. Hsp104A503V, Hsp104A503S, and Hsp104A503V-DPLF rescued α-syn toxicity in Dire1 and Datg8 strains (FIG. 4D). Thus, the UPR and autophagy are not required for rescue.

Hsp104A503V eliminated cytoplasmic α-syn inclusions and restored plasma membrane α-syn localization, whereas Hsp104WT had no effect (FIG. 4E). Indeed, Hsp104A503V reduced the amount of insoluble α-syn by ~66%, whereas Hsp104WT increased it by ~33.9% (FIG. 4F). Thus, potentiated Hsp104 variants eradicate α-syn inclusions and restore α-syn localization.

6. Potentiated Hsp104 Variants Prevent Neurodegeneration in a *C. elegans* PD Model.

To test potentiated Hsp104 variants in a metazoan nervous system, we used a transgenic *C. elegans* PD model, which has illuminated mechanisms and modifiers of α-syn-induced neurodegeneration (Cao et al., 2005; Cooper et al., 2006; Tardiff et al., 2013). We selected Hsp104A503S and Hsp104A503V-DPLF to study in this context, which displayed strong (Hsp104A503S) and moderate (Hsp104A503V-DPLF) rescue of α-syn toxicity (FIG. 4A). We focused on these variants because unlike Hsp104A503V they conferred greater than WT levels of thermotolerance and were less toxic to yeast at 37° C. when expressed from the galactose promoter (FIGS. 12A and 12B).

The dopamine transporter (dat-1) gene promoter was used to direct expression of Hsp104 variants and α-syn to dopaminergic (DA) neurons. Expression of α-syn alone resulted in ~16% of animals with normal numbers of DA neurons after 7 days and 8% of animals after 10 days compared to controls (FIGS. 5A-5C). Coexpression of Hsp104WT or an ATPase-dead, substrate binding-deficient Hsp104DPLA-DWB (which bears the "double pore loop" and "double Walker B" mutations: Y257A:E285Q:Y662A:E687Q) did not rescue neurodegeneration (FIGS. 5A and 5B). *C. elegans* expressing Hsp104A503S or Hsp104A503V-DPLF displayed significant protection (30.5% and 34% normal worms, respectively) compared to the null Hsp104 variant or α-syn alone at day 7 (FIG. 5A). This trend continued at day 10 (FIG. 5B), when Hsp104A503S-expressing (21%) and Hsp104A503V-DPLF-expressing (24%) worms had significantly more normal DA neurons compared to α-syn alone (7.8%), Hsp104DPLA-DWB (10%), or Hsp104WT (11%). Hsp104 variants did not alter α-syn mRNA levels (FIG. 12C). Thus, Hsp104A503S and Hsp104A503V-DPLF remain significantly neuroprotective against α-syn toxicity even as animals age.

7. Potentiated Hsp104 Variants Typically Have Elevated ATPase Activity.

Nearly all of the Hsp104A503X variants suppressed α-syn, FUS, and TDP-43 toxicity in yeast. This unexpected degeneracy is intriguing as there are few, if any, examples of missense mutations to nearly any class of residue that lead to a therapeutic gain of function. To explore the mechanism behind this gain of function, we assessed the biochemical properties of several Hsp104 variants that suppressed toxicity. Each Hsp104A503X variant and Hsp104Y507C exhibited ~2- to 4-fold higher ATPase activity than Hsp104WT (FIG. 6A). Hsp104D498V has higher ATPase activity than Hsp104WT, though not as high as the Hsp104A503X variants (FIG. 6A). Hsp104D504C had ATPase activity similar to Hsp104WT (FIG. 6A). Thus, enhanced Hsp104 variants typically have higher ATPase activity than Hsp104WT. However, Hsp104D504C illustrates that elevated ATPase activity is not absolutely required for potentiation.

8. Potentiated Hsp104 Variants Do Not Require Hsp70 and Hsp40 for Disaggregation.

Rescue of toxicity by enhanced Hsp104 variants might reflect an altered mechanism of disaggregation. Thus, we assessed activity against disordered luciferase aggregates (DeSantis et al., 2012). Hsp104WT was inactive alone and required Hsp70 and Hsp40, which could be from human (Hsc70 and Hdj2) or yeast (Ssa1 and Ydj1; FIGS. 6B and 6C). By contrast, potentiated Hsp104 variants were extremely active without Hsp70 and Hsp40, and with the exception of Hsp104D504C, Hsc70 and Hdj2 further increased activity (FIGS. 6B and 6C). Typically, in the absence of Hsc70 and Hdj2, potentiated Hsp104 variants were ~3- to 9-fold more active than Hsp104WT plus Hsc70 and Hdj2 (FIG. 6B). The only exception was Hsp104D498V, which in the absence of Hsc70 and Hdj2 was still as active as Hsp104WT plus Hsc70 and Hdj2 (FIG. 6B). Hsp104WT was most active in the presence of Ssa1, Ydj1, and the Hsp110, Sse1 (FIG. 6C) (Shorter, 2011). However, even here, Hsp104WT luciferase reactivation activity only reached Hsp104A503V, Hsp104A503S, and Hsp104A503V-DPLF activity in the absence of Ssa1, Ydj1, and Sse1 (FIG. 6C). In the presence of Ssa1, Ydj1, and Sse1, the luciferase reactivation activity of Hsp104A503V, Hsp104A503S, and Hsp104A503V-DPLF was ~7- to 8-fold higher than Hsp104WT (FIG. 6C). Potentiated Hsp104 variants are highly active without Hsp70 and Hsp40 (FIGS. 6B and 6C). Thus, absolute dependence on Hsp70 and Hsp40 hinders Hsp104 from rescuing α-syn, FUS, and TDP-43 toxicity. Independence from Hsp70 and Hsp40 is promising for applying Hsp104 variants to reverse protein misfolding in diverse systems, such as purification of aggregation-prone recombinant proteins from *E. coli* where DnaK incompatibility is an issue (DeSantis and Shorter, 2012).

9. Potentiated Hsp104 Variants Translocate Substrate Faster Than Hsp104WT.

We next determined that potentiated Hsp104 variants displayed accelerated substrate translocation. Thus, we used an Hsp104 variant, termed HAP, where G739-K741 are mutated to IGF, which enables association with the chambered peptidase ClpP (Tessarz et al., 2008). In the presence of ClpP, translocated substrates are degraded rather than released. Thus, HAP translocates fluorescein isothiocyanate (FITC)-casein for degradation by ClpP, thereby releasing FITC and increasing fluorescence. In the presence of ClpP, HAPA503V ($K_m$ ~1.29 μM) is a more effective FITC-casein translocase than HAPWT ($K_m$ ~2.88 μM) (FIG. 6D). The lower $K_m$ for HAPA503V might reflect differences in substrate recognition rather than translocation speed. However, the $K_d$ of Hsp104WT (Kd ~65 nM) and Hsp104A503V ($K_d$ ~80 nM) for FITC-casein were similar (FIG. 6E) as were binding kinetics (FIG. 6F). Thus, substrate recognition by Hsp104WT and Hsp104A503V is very similar. Hence, we suggest that Hsp104A503V translocates substrate more rapidly than Hsp104WT. Accelerated translocation likely enables potentiated variants to avoid kinetic traps and exert additional force to unfold stable substrates.

10. Potentiated Hsp104 Variants Are Enhanced Unfoldases.

Next, we established that enhanced Hsp104 variants had enhanced unfoldase activity using a RepA1-70-GFP substrate (Doyle et al., 2007). To assess RepA1-70-GFP unfolding in the absence of spontaneous refolding, we added GroELtrap, which captures unfolded proteins and prevents refolding (Weber-Ban et al., 1999). Hsp104WT unfolds RepA1-70-GFP, but only in the presence of a permissive ratio of ATP and ATPgS (Doyle et al., 2007)(FIGS. 6G and 6H). Thus, with ATP alone, Hsp104WT did not unfold RepA1-70-GFP (FIG. 6G). By contrast, Hsp104A503X variants rapidly unfolded RepA1-70-GFP in the presence of ATP (FIG. 6G). Hsp104WT unfolded RepA1-70-GFP in the presence of an ATP:ATPgS (3:1) mixture. By contrast, ATP: ATPgS slightly inhibited Hsp104A503V unfoldase activity, but even here, Hsp104A503V unfolded RepA1-70-GFP more rapidly than Hsp104WT (FIG. 6G). Hsp104A503X variants had very similar unfoldase kinetics (FIG. 6G). By contrast, Hsp104D498V, Hsp104D504C, and Hsp104A503V-DPLF were slightly slower unfoldases than Hsp104A503V, whereas Hsp104Y507C was slightly faster (FIG. 6H). These differences could reflect changes in substrate recognition or turnover or both. Regardless, potentiated Hsp104 variants are enhanced unfoldases that are intrinsically primed to unfold substrates and do not have to wait for regulatory events (mimicked here by ATPgS addition).

11. Hsp104A503V Hexamers Are Tuned Differently Than Hsp104WT Hexamers.

Do potentiated Hsp104 variants employ the same mechanism of intersubunit collaboration as Hsp104WT to disaggregate proteins? How Hsp104 subunits within the hexamer collaborate to promote disaggregation can be interrogated via mutant subunit doping. Here, mutant subunits defective in ATP hydrolysis, substrate binding, or both are mixed with WT subunits to generate heterohexamer ensembles according to the binomial distribution (DeSantis et al., 2012). Hsp104 forms dynamic hexamers that exchange subunits on the minute timescale, which ensures statistical incorporation of mutant subunits (DeSantis et al., 2012). The disaggregase activity of various heterohexamer ensembles enables determination of the number of mutant subunits that inactivate the WT hexamer. Thus, we can determine if subunit collaboration within Hsp104 hexamers is probabilistic (six mutant subunits are required to abolish activity), subglobally cooperative (two to five mutant subunits abolish activity), or globally cooperative (one mutant subunit abolishes activity) (DeSantis et al., 2012). Incorporation of Hsp104A503V-DWA subunits (which bear the "double Walker A" [DWA] K218T:K620T mutations and cannot bind ATP) or Hsp104A503V-DPLA subunits (which bear the "double pore loop" [DPL] Y257A:Y662A mutations and cannot bind substrate) into Hsp104A503V hexamers caused a roughly linear decline in luciferase disaggregase activity (FIG. 6I). This linear decline indicates that, like Hsp104WT, Hsp104A503V hexamers resolve disordered aggregates via a probabilistic mechanism (DeSantis et al., 2012). Thus, a single Hsp104A503V subunit per hexamer able to hydrolyze ATP and engage substrate can drive disaggregation.

However, Hsp104A503V hexamers operate differently than Hsp104WT hexamers. A single Hsp104DWB subunit (which bears the "double Walker B" [DWB] E285Q:E687Q mutations and can bind but not hydrolyze ATP) inactivates the Hsp104WT hexamer (DeSantis et al., 2012). By contrast, the luciferase disaggregase activity of Hsp104A503V was stimulated by Hsp104A503V-DWB sub-units (FIG. 6J). Fluorescence resonance energy transfer (FRET) studies confirmed that Hsp104A503V-DWB subunits incorporated into Hsp104A503V hexamers. The FRET efficiency was 0.36 (compared to 0.38 for mixing Hsp104WT with Hsp104DWB; DeSantis et al., 2012) using the conditions employed for luciferase reactivation. In high-salt buffer (1 M NaCl), hexamerization is inhibited and FRET efficiency decreased to 0.24. At a higher Hsp104 concentration (1 mM), which favors hexamerization, FRET efficiency increased to 0.43. We could model the stimulatory effect of Hsp104A503V-DWB subunits if we imposed rules whereby an Hsp104A503V-DWB subunit stimulates activity of an adjacent Hsp104A503V subunit ~2-fold (FIG. 6J). This stimulation depended on substrate binding by Hsp104A503V-DWB as Hsp104A503V-DPLA-DWB subunits (which bear the "double pore loop" and DWB Y257A:E285Q:Y662A:E687Q mutations and can bind, but not hydrolyze, ATP and cannot bind substrate) failed to stimulate adjacent Hsp104A503V subunits (FIG. 6J). Thus, Hsp104A503V hexamers operate via principles distinct from those of Hsp104WT hexamers. The Hsp104A503V hexamer displays greater plasticity and tolerates a wider variety of subunit-inactivating events to maintain a robust disaggregase activity. Thus, an Hsp104A503V subunit that (1) binds but cannot hydrolyze ATP and (2) engages substrate stimulates the disaggregase activity of an adjacent Hsp104A503V subunit. In Hsp104WT, a single subunit with these properties inactivates the hexamer. The increased resilience of Hsp104A503V hexamers to subunit-inactivating events likely empowers facile resolution of recalcitrant substrates.

12. Hsp104A503V, Hsp104A503S, and Hsp104A503V-DPLF Disaggregate Preformed α-syn Fibrils More Efficaciously Than Hsp104WT.

To test Hsp104A503V, Hsp104A503S, and Hsp104A503V-DPLF in comparison to Hsp104WT against a recalcitrant PD-associated substrate we employed α-syn fibrils, allowing us to distinguish if Hsp104 prevented amyloid formation or eliminated preformed amyloid. Hsp104A503V, Hsp104A503S, and Hsp104A503V-DPLF dis-aggregated preformed α-syn fibrils at concentrations where Hsp104WT was inactive (FIGS. 7A-7C). Indeed, electron microscopy (EM) revealed that α-syn fibrils were converted to small structures by low concentrations of Hsp104A503V, Hsp104A503S, and Hsp104A503V-DPLF, whereas Hsp104WT left fibrils intact (FIG. 7C). Thus, Hsp104A503V, Hsp104A503S, and Hsp104A503V-DPLF are more powerful amyloid disaggregases than Hsp104WT.

13. Hsp104A503V and Hsp104A503S Disaggregate Preformed TDP-43 and FUS Aggregates More Efficaciously Than Hsp104WT.

Figure 7D:
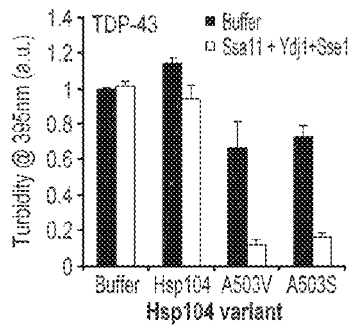
Figure 7E:
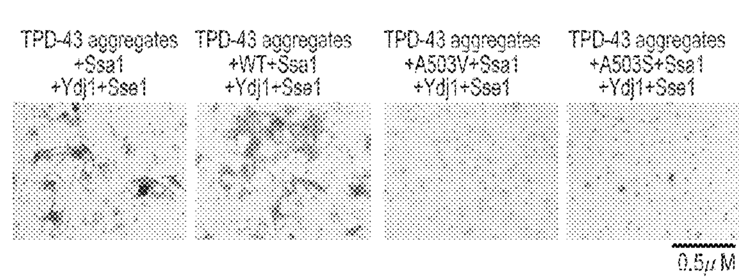

Next, we tested whether Hsp104A503V and Hsp104A503S were more potent disaggregases of TDP-43 and FUS (Johnson et al., 2009; Sun et al., 2011). Hsp104WT was unable to resolve TDP-43 aggregates and slightly enhanced TDP-43 aggregation in the absence of Ssa1, Ydj1, and Sse1 (FIG. 7D). By contrast, Hsp104A503V and Hsp104A503S partially resolved TDP-43 aggregates in the absence of Ssa1, Ydj1, and Sse1 (FIG. 7D). Hsp104A503V and Hsp104A503S in the presence of Ssa1, Ydj1, and Sse1, but not Hsp104WT, effectively dissolved short TDP-43 filaments and amorphous structures (FIGS. 7D and 7E).

Figure 7F:
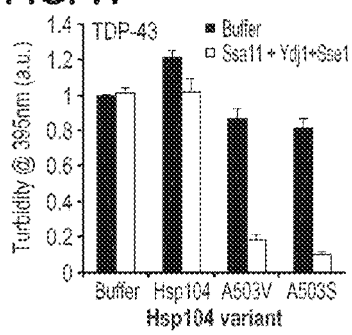
Figure 7G:
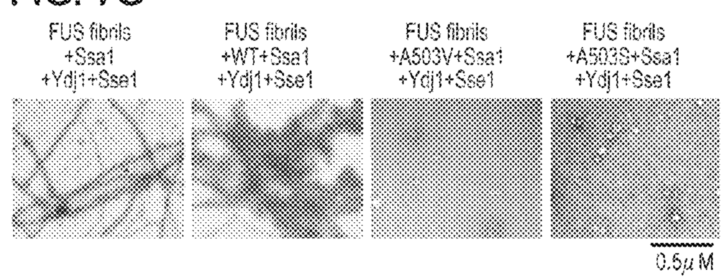

Very similar results were obtained with preformed FUS fibrils (FIGS. 7F and 7G). Hsp104WT slightly increased FUS aggregation in the absence of Ssa1, Ydj1, and Sse1, whereas Hsp104A503V and Hsp104A503S modestly reduced aggregation (FIG. 7F). Hsp104A503V and Hsp104A503S effectively disaggregated FUS in the presence of Ssa1, Ydj1, and Sse1, whereas Hsp104WT was ineffective (FIG. 7F). Indeed, Hsp104A503V and Hsp104A503S eradicated FUS fibrils (FIG. 7G). Thus, Hsp104A503V and Hsp104A503S disaggregate preformed TDP-43 and FUS aggregates more efficaciously than Hsp104WT.

Example 2

Rat Model

Recombinant proteins are prepared/expressed as discussed in Example 1 and/or as otherwise described in the specification. The methodology of Lo Bianco, C.; Shorter, J. et al. (J. Clin. Invest. September 2008) is employed.

Mutations and/or combinations of mutations as taught above are identified as useful in preventing, reducing, or eliminating aggregation of one or more proteins involved in a neurodegenerative process or disease.

REFERENCES

Berkowitz, L. A., Hamamichi, S., Knight, A. L., Harrington, A. J., Caldwell, G. A., and Caldwell, K. A. (2008a). Application of a *C. elegans* dopamine neuron degen-eration assay for the validation of potential Parkinson's disease genes. J. Vis. Exp. 17, 835.

Berkowitz, L. A., Knight, A. L., Caldwell, G. A., and Caldwell, K. A. (2008b). Generation of stable transgenic *C. elegans* using microinjection. J. Vis. Exp. 18, 833.

Cabantous, S., and Waldo, G. S. (2006). In vivo and in vitro protein solubility assays using split GFP. Nat. Methods 3, 845-854.

Cao, S., Gelwix, C. C., Caldwell, K. A., and Caldwell, G. A. (2005). Torsin-mediated protection from cellular stress in the dopaminergic neurons of *Caenorhabditis elegans*. J. Neurosci. 25, 3801-3812.

Cooper, A. A., Gitler, A. D., Cashikar, A., Haynes, C. M., Hill, K. J., Bhullar, B., Liu, K., Xu, K., Strathearn, K. E., Liu, F., et al. (2006). Alphα-synuclein blocks ER-Golgi traffic and Rab1 rescues neuron loss in Parkinson's models. Science 313, 324-328.

Cushman, M., Johnson, B. S., King, O. D., Gitler, A. D., and Shorter, J. (2010). Prion-like disorders: blurring the divide between transmissibility and infectivity. J. Cell Sci. 123, 1191-1201.

Cushman-Nick, M., Bonini, N. M., and Shorter, J. (2013). Hsp104 suppresses polyglutamine-induced degeneration post onset in a *Drosophila* MJD/SCA3 model. PLoS Genet. 9, e1003781.

DeSantis, M. E., and Shorter, J. (2012). The elusive middle domain of Hsp104 and ClpB: location and function. Biochim. Biophys. Acta 1823, 29-39.

DeSantis, M. E., Leung, E. H., Sweeny, E. A., Jackrel, M. E., Cushman-Nick, M., Neuhaus-Follini, A., Vashist, S., Sochor, M. A., Knight, M. N., and Shorter, J. (2012). Operational plasticity enables hsp104 to disaggregate diverse amyloid and nonamyloid clients. Cell 151, 778-793.

Doyle, S. M., Shorter, J., Zolkiewski, M., Hoskins, J. R., Lindquist, S., and Wickner, S. (2007). Asymmetric deceleration of ClpB or Hsp104 ATPase activ-ity unleashes protein-remodeling activity. Nat. Struct. Mol. Biol. 14, 114-122.

Duennwald, M. L., Echeverria, A., and Shorter, J. (2012). Small heat shock proteins potentiate amyloid dissolution by protein disaggregases from yeast and humans. PLoS Biol. 10, e1001346.

Elden, A. C., Kim, H. J., Hart, M. P., Chen-Plotkin, A. S., Johnson, B. S., Fang, X., Armakola, M., Geser, F., Greene, R., Lu, M. M., et al. (2010). Ataxin-2 interme-diate-length polyglutamine expansions are associated with increased risk for ALS. Nature 466, 1069-1075.

Gietz, R. D., and Schiestl, R. H. (2007). High-efficiency yeast transformation using the LiAc/SS carrier DNA/PEG method. Nat. Protoc. 2, 31-34.

Glover, J. R., and Lindquist, S. (1998). Hsp104, Hsp70, and Hsp40: a novel chaperone system that rescues previously aggregated proteins. Cell 94, 73-82.

Harrington, A. J., Yacoubian, T. A., Slone, S. R., Caldwell, K. A., and Caldwell, G. A. (2012). Functional analysis of VPS41-mediated neuroprotection in *Caenorhabditis elegans* and mammalian models of Parkinson's disease. J. Neurosci. 32, 2142-2153.

Jackrel, M. E., DeSantis, M. E., Martinez, B. A., Castellano, L. M., Stewart, R. M., Caldwell, K. A., Caldwell, G. A., Shorter, J. (2014). Potentiated Hsp104 Variants Antagonize Diverse Proteotoxic Misfolding Events. Cell. 156:170-182 and S1-S10.

Johnson, B. S., McCaffery, J. M., Lindquist, S., and Gitler, A. D. (2008). A yeast TDP-43 proteinopathy model: Exploring the molecular determinants of TDP-43 aggregation and cellular toxicity. Proc. Natl. Acad. Sci. USA 105, 6439-6444.

Johnson, B. S., Snead, D., Lee, J. J., McCaffery, J. M., Shorter, J., and Gitler, A. D. (2009). TDP-43 is intrinsically aggregation-prone, and amyotrophic lateral sclerosis-linked mutations accelerate aggregation and increase toxicity. J. Biol. Chem. 284, 20329-20339.

Ju, S., Tardiff, D. F., Han, H., Divya, K., Zhong, Q., Maquat, L. E., Bosco, D. A., Hayward, L. J., Brown, R. H., Jr., Lindquist, S., et al. (2011). A yeast model of FUS/TLS-dependent cytotoxicity. PLoS Biol. 9, el001052.

Lipinska, N., Zie, tkiewicz, S., Sobczak, A., Jurczyk, A., Potocki, W., Morawiec, E., Wawrzycka, A., Gumowski, K., Slusarz, M., Rodziewicz-Motowidlo, S., et al. (2013). Disruption of ionic interactions between the nucleotide binding domain 1 (NBD1) and middle (M) domain in Hsp100 disaggregase unleashes toxic hyperactivity and partial independence from Hsp70. J. Biol. Chem. 288, 2857-2869.

Lo Bianco, C., Shorter, J., Regulier, E., Lashuel, H., Iwatsubo, T., Lindquist, S., and Aebischer, P. (September 2008). Hsp104 antagonizes α-synuclein aggregation and reduces dopaminergic degeneration in a rat model of Parkinson disease. J. Clin. Invest. 118, 3087-3097.

Moreau, M. J., McGeoch, A. T., Lowe, A. R., Itzhaki, L. S., and Bell, S. D. (2007). ATPase site architecture and helicase mechanism of an archaeal MCM. Mol. Cell 28, 304-314.

Newby, G. A., and Lindquist, S. (2013). Blessings in disguise: biological benefits of prion-like mechanisms. Trends Cell Biol. 23, 251-259. Chaperone Coexpression Plasmids: Differential and Synergistic Roles of DnaK-DnaJ-GrpE and GroEL-GroES in Assisting Folding of an Allergen of Japanese Cedar Pollen, Cryj2, in *Escherichia coli*. Appl. Environ. Microbiol 64(5):1694-1699.

Nishihara, K., et al. (May 1998).

Outeiro, T. F., and Lindquist, S. (2003). Yeast cells provide insight into alpha-synuclein biology and pathobiology. Science 302, 1772-1775.

Raviol, H., Bukau, B., and Mayer, M. P. (2006). Human and yeast Hsp110 chaperones exhibit functional differences. FEBS Lett. 580, 168-174.

Robberecht, W., and Philips, T. (2013). The changing scene of amyotrophic lateral sclerosis. Nat. Rev. Neurosci. 14, 248-264.

Saibil, H. (2013). Chaperone machines for protein folding, unfolding and disaggregation. Nat. Rev. Mol. Cell Biol. 14, 630-642.

Sanchez, Y., and Lindquist, S. L. (1990). HSP104 required for induced thermotolerance. Science 248, 1112-1115.

Schirmer, E. C., Homann, O. R., Kowal, A. S., and Lindquist, S. (2004). Dominant gain-of-function mutations in Hsp104p reveal crucial roles for the middle region. Mol. Biol. Cell 15, 2061-2072.

Shorter, J. (2008). Hsp104: a weapon to combat diverse neurodegenerative disorders. Neurosignals 16, 63-74.

Shorter, J. (2011). The mammalian disaggregase machinery: Hsp110 synergizes with Hsp70 and Hsp40 to catalyze protein disaggregation and reactivation in a cell-free system. PLoS ONE 6, e26319.

Shorter, J., and Lindquist, S. (2008). Hsp104, Hsp70 and Hsp40 interplay regulates formation, growth and elimination of Sup35 prions. EMBO J. 27, 2712-2724. Sun, Z., Diaz, Z., Fang, X., Hart, M. P., Chesi, A., Shorter, J., and Gitler, A. D. (2011). Molecular determinants and genetic modifiers of aggregation and toxicity for the ALS disease protein FUS/TLS. PLoS Biol. 9, e1000614.

Tardiff, D. F., Jui, N. T., Khurana, V., Tambe, M. A., Thompson, M. L., Chung, C. Y., Kamadurai, H. B., Kim, H. T., Lancaster, A. K., Caldwell, K. A., et al. (2013). Yeast reveal a "druggable" RspS/Nedd4 network that ameliorates alpha-synuclein toxicity in neurons. Science 342, 979-983.

Tessarz, P., Mogk, A., and Bukau, B. (2008). Substrate threading through the central pore of the Hsp104 chaperone as a common mechanism for protein disaggregation and prion propagation. Mol. Microbiol. 68, 87-97.

Vacher, C., Garcia-Oroz, L., and Rubinsztein, D. C. (2005). Overexpression of yeast hsp104 reduces polyglutamine aggregation and prolongs survival of a transgenic mouse model of Huntington's disease. Hum. Mol. Genet. 14, 3425-3433.

Weber-Ban, E. U., Reid, B. G., Miranker, A. D., and Horwich, A. L. (1999). Global unfolding of a substrate protein by the Hsp100 chaperone ClpA. Nature 401, 90-93.

Werbeck, N. D., Schlee, S., and Reinstein, J. (2008). Coupling and dynamics of subunits in the hexameric AAA+ chaperone ClpB. J. Mol. Biol. 378, 178-190.

All publications, patents, and patent applications cited in this application are hereby incorporated by reference in their entireties as if each individual publication, patent or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications can be made thereto without departing from the spirit or scope of the appended claims.

The invention claimed is:

1. A recombinant Hsp104 protein of wild type amino acid sequence of SEQ ID NO: 1, wherein said sequence comprises a missense mutation, wherein said missense mutation is A503C, A503D, A503E, A503F, A503G, A503H, A503I, A503K, A503L, A503M, A503N, A503Q, A503R, A503S, A503T, A503V, A503W, or A503Y, wherein said sequence further comprises mutation in the substrate-binding pore loops where said mutation in the substrate binding loop comprises a Y257F and Y662F.

2. The recombinant protein of claim 1, wherein said missense mutation is A503C, A503G, A503S, or A503V.

3. A recombinant Hsp104 protein of wild type amino acid sequence of SEQ ID NO: 1, wherein said sequence comprises mutations A503V, Y257F, and Y662F.

4. A method for suppressing proteotoxicity in a mammal in need thereof, comprising administering the recombinant protein of claim 1.

5. A composition comprising the recombinant protein of claim 1 and a pharmaceutically acceptable carrier.

6. A method for suppressing proteotoxicity in a mammal in need thereof, comprising administering the composition of claim 5.

7. A method for suppressing proteotoxicity in a mammal in need thereof, comprising administering the recombinant protein of claim 2.

8. A composition comprising the recombinant protein of claim 2 and a pharmaceutically acceptable carrier.

9. A method for suppressing proteotoxicity in a mammal in need thereof, comprising administering the composition of claim 8.

10. A method for suppressing proteotoxicity in a mammal in need thereof, comprising administering the recombinant protein of claim 3.

11. A composition comprising the recombinant protein of claim 3 and a pharmaceutically acceptable carrier.

12. A method for suppressing proteotoxicity in a mammal in need thereof, comprising administering the composition of claim 11.

13. The recombinant protein of claim 2, wherein said missense mutation is A503S.

14. The recombinant protein of claim 13, wherein said sequence comprises mutations Y257F and Y662F.

15. A method for suppressing proteotoxicity in a mammal in need thereof, comprising administering the recombinant protein of claim 13.

16. A composition comprising the recombinant protein of claim 13 and a pharmaceutically acceptable carrier.

17. A method for suppressing proteotoxicity in a mammal in need thereof, comprising administering the composition of claim 16.

* * * * *

UNITED STATES PATENT AND TRADEMARK OFFICE

CERTIFICATE OF CORRECTION

PATENT NO. : 9,994,625 B2
APPLICATION NO. : 14/630785
DATED : June 12, 2018
INVENTOR(S) : James Shorter and Meredith E. Jackrel It is certified that error appears in the above-identified patent and that said Letters Patent is hereby corrected as shown below:

In the Specification

Column 1, the paragraph immediately following the heading "STATEMENT REGARDING FEDERALLY SPONSORED RESEARCH OR DEVELOPMENT" is replaced with the following paragraph:
-- This invention was made with government support under grant numbers OD002177, NS067354, HD074510, and GM099836 awarded by the National Institutes of Health. The government has certain rights in the invention. --

Signed and Sealed this
Thirtieth Day of July, 2019

Andrei Iancu
*Director of the United States Patent and Trademark Office*